United States Patent
Washburn et al.

(10) Patent No.: US 6,936,590 B2
(45) Date of Patent: *Aug. 30, 2005

(54) C-ARYL GLUCOSIDE SGLT2 INHIBITORS AND METHOD

(75) Inventors: William N. Washburn, Titusville, NJ (US); Bruce Ellsworth, Princeton, NJ (US); Wei Meng, Pennington, NJ (US); Gang Wu, Princeton, NJ (US); Philip M. Sher, Plainsboro, NJ (US)

(73) Assignee: Bristol Myers Squibb Company, Princeton, NJ (US)

( * ) Notice: Subject to any disclaimer, the term of this patent is extended or adjusted under 35 U.S.C. 154(b) by 1 day.

This patent is subject to a terminal disclaimer.

(21) Appl. No.: 10/264,410

(22) Filed: Oct. 4, 2002

(65) Prior Publication Data

US 2003/0114390 A1 Jun. 19, 2003

Related U.S. Application Data

(63) Continuation of application No. 09/805,341, filed on Mar. 13, 2001, now abandoned.

(51) Int. Cl.$^7$ .............................................. A61K 31/70
(52) U.S. Cl. ........................................................ 514/25
(58) Field of Search ........................................... 514/25

(56) References Cited

U.S. PATENT DOCUMENTS

| | | | |
|---|---|---|---|
| 5,444,050 A | | 8/1995 | Kogan et al. |
| 6,414,126 B1 | * | 7/2002 | Ellsworth et al. .......... 536/17.2 |
| 6,515,117 B2 | * | 2/2003 | Ellsworth et al. .......... 536/17.2 |

FOREIGN PATENT DOCUMENTS

| | | | |
|---|---|---|---|
| DE | 3632536 A1 | 9/1986 |
| EP | 0 598359 A1 | 5/1994 |
| EP | 0 684 254 B1 | 11/1995 |
| EP | 0 773 226 B1 | 5/1997 |
| EP | 0 850 948 A1 | 1/1998 |
| EP | 0 997472 A2 | 5/2000 |
| JP | 9124684 | 11/1995 |
| JP | 9124685 | 11/1995 |
| JP | 8-27006 | 1/1996 |
| JP | 9188625 | 11/1996 |
| JP | 10245391 | 3/1997 |
| JP | WO 01/16147 A1 | 3/2001 |
| WO | WO 97/01335 | 1/1997 |
| WO | WO 9831697 A | 7/1998 |
| WO | WO 0 018918 | 4/2000 |

OTHER PUBLICATIONS

T. Kuribayashi et al., Journal of Carbohydrate Chemistry, (1999) vol. 18, No. 4, pp. 371–382.
W. Gaffield et al., Tetrahedron, (1978) vol. 34, No. 20, pp. 3089–3096.
Benhaddou et al. Carbohydrate Research 260 (1994) pp. 243–250.
Hongu et al. Chemical Phar. Bull. (1998) vol. 46, No. 10, pp. 1545–1555.
Tsujihara et al. Chemical Pharm. Bull. (1996) vol. 44. No. 6. pp. 1174–1180.
Hongu et al. Chem. Pharm. Bull. (1998) vol. 46. No. 1, pp. 22–23.
Oku et al. Diabetes. vol. 48 (1999) pp. 1794–1800.

* cited by examiner

Primary Examiner—San-Ming Hui
(74) Attorney, Agent, or Firm—Jonathan N. Provoost; Burton Rodney

(57) ABSTRACT

A method is provided for treating diabetes and related diseases employing an SGLT2 inhibiting amount of a compound of the formula

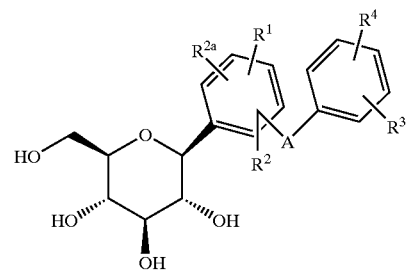

alone or in combination with one or more other antidiabetic agent(s) or other therapeutic agent(s).

9 Claims, No Drawings

C-ARYL GLUCOSIDE SGLT2 INHIBITORS AND METHOD

This application is a Continuation under 37 C.F.R. § 1.53(b) of U.S. Ser. No. 09/805,341, filed Mar. 13, 2001, now abandoned.

FIELD OF THE INVENTION

The present invention relates to the use of C-aryl glucosides which are inhibitors of sodium dependent glucose transporters found in the intestine and kidney (SGLT2) and specifically to a method for treating diabetes, especially type II diabetes, as well as hyperglycemia, hyperinsulinemia, obesity, hypertriglyceridemia, Syndrome X, diabetic complications, atherosclerosis and related diseases, employing such C-aryl glucosides alone or in combination with one, two or more other type antidiabetic agent and/or one, two or more other type therapeutic agents such as hypolipidemic agents.

BACKGROUND OF THE INVENTION

Approximately 100 million people worldwide suffer from type II diabetes (NIDDM), which is characterized by hyperglycemia due to excessive hepatic glucose production and peripheral insulin resistance, the root causes for which are as yet unknown. Hyperglycemia is considered to be the major risk factor for the development of diabetic complications, and is likely to contribute directly to the impairment of insulin secretion seen in advanced NIDDM. Normalization of plasma glucose in NIDDM patients would be predicted to improve insulin action, and to offset the development of diabetic complications. An inhibitor of the sodium-dependent glucose transporter SGLT2 in the kidney would be expected to aid in the normalization of plasma glucose levels, and perhaps body weight, by enhancing glucose excretion.

The development of novel, safe, and orally active antidiabetic agents is also desired in order to complement existing therapies, including the sulfonylureas, thiazolidinediones, metformin, and insulin, and to avoid the potential side effects associated with the use of these other agents.

Hyperglycemia is a hallmark of type II diabetes (NIDDM); consistent control of plasma glucose levels in diabetes can offset the development of diabetic complications and beta cell failure seen in advanced disease. Plasma glucose is normally filtered in the kidney in the glomerulus and actively reabsorbed in the proximal tubule. SGLT2 appears to be the major transporter responsible for the reuptake of glucose at this site. The SGLT specific inhibitor phlorizin or closely related analogs inhibit this reuptake process in diabetic rodents and dogs resulting in normalization of plasma glucose levels by promoting glucose excretion without hypoglycemic side effects. Long term (6 month) treatment of Zucker diabetic rats with an SGLT2 inhibitor has been reported to improve insulin response to glycemia, improve insulin sensitivity, and delay the onset of nephropathy and neuropathy in these animals, with no detectable pathology in the kidney and no electrolyte imbalance in plasma. Selective inhibition of SGLT2 in diabetic patients would be expected to normalize plasma glucose by enhancing the excretion of glucose in the urine, thereby improving insulin sensitivity, and delaying the development of diabetic complications.

Ninety percent of glucose reuptake in the kidney occurs in the epithelial cells of the early S1 segment of the renal cortical proximal tubule, and SGLT2 is likely to be the major transporter responsible for this reuptake. SGLT2 is a 672 amino acid protein containing 14 membrane-spanning segments that is predominantly expressed in the early S1 segment of the renal proximal tubules. The substrate specificity, sodium dependence, and localization of SGLT2 are consistent with the properties of the high capacity, low affinity, sodium-dependent glucose transporter previously characterized in human cortical kidney proximal tubules. In addition, hybrid depletion studies implicate SGLT2 as the predominant $Na^+$/glucose cotransporter in the S1 segment of the proximal tubule, since virtually all Na-dependent glucose transport activity encoded in mRNA from rat kidney cortex is inhibited by an antisense oligonucleotide specific to rat SGLT2. SGLT2 is a candidate gene for some forms of familial glucosuria, a genetic abnormality in which renal glucose reabsorption is impaired to varying degrees. None of these syndromes investigated to date map to the SGLT2 locus on chromosome 16. However, the studies of highly homologous rodent SGLTs strongly implicate SGLT2 as the major renal sodium-dependent transporter of glucose and suggest that the glucosuria locus that has been mapped encodes an SGLT2 regulator. Inhibition of SGLT2 would be predicted to reduce plasma glucose levels via enhanced glucose excretion in diabetic patients.

SGLT1, another Na-dependent glucose cotransporter that is 60% identical to SGLT2 at the amino acid level, is expressed in the small intestine and in the more distal S3 segment of the renal proximal tubule. Despite their sequence similarities, human SGLT1 and SGLT2 are biochemically distinguishable. For SGLT1, the molar ratio of $Na^+$ to glucose transported is 2:1, whereas for SGLT2, the ratio is 1:1. The $K_m$ for $Na^+$ is 32 and 250–300 mM for SGLT1 and SGLT2, respectively. $K_m$ values for uptake of glucose and the nonmetabolizable glucose analog α-methyl-D-glucopyranoside (AMG) are similar for SGLT1 and SGLT2, i.e. 0.8 and 1.6 mM (glucose) and 0.4 and 1.6 mM (AMG) for SGLT1 and SGLT2 transporters, respectively. However, the two transporters do vary in their substrate specificities for sugars such as galactose, which is a substrate for SGLT1 only.

Administration of phlorizin, a specific inhibitor of SGLT activity, provided proof of concept in vivo by promoting glucose excretion, lowering fasting and fed plasma glucose, and promoting glucose utilization without hypoglycemic side effects in several diabetic rodent models and in one canine diabetes model. No adverse effects on plasma ion balance, renal function or renal morphology have been observed as a consequence of phlorizin treatment for as long as two weeks. In addition, no hypoglycemic or other adverse effects have been observed when phlorizin is administered to normal animals, despite the presence of glycosuria. Administration of an inhibitor of renal SGLTs for a 6-month period (Tanabe Seiyaku) was reported to improve fasting and fed plasma glucose, improve insulin secretion and utilization in obese NIDDM rat models, and offset the development of nephropathy and neuropathy in the absence of hypoglycemic or renal side effects.

Phlorizin itself is unattractive as an oral drug since it is a nonspecific SGLT1/SGLT2 inhibitor that is hydrolyzed in the gut to its aglycone phloretin, which is a potent inhibitor of facilitated glucose transport. Concurrent inhibition of facilitative glucose transporters (GLUTs) is undesirable since such inhibitors would be predicted to exacerbate peripheral insulin resistance as well as promote hypoglycemia in the CNS. Inhibition of SGLT1 could also have serious adverse consequences as is illustrated by the hereditary syndrome glucose/galactose malabsorption (GGM), in which mutations in the SGLT1 cotransporter result in impaired glucose uptake in the intestine, and life-threatening diarrhea and dehydration. The biochemical differences between SGLT2 and SGLT1, as well as the degree of sequence divergence between them, allow for identification of selective SGLT2 inhibitors.

The familial glycosuria syndromes are conditions in which intestinal glucose transport, and renal transport of other ions and amino acids, are normal. Familial glycosuria patients appear to develop normally, have normal plasma glucose levels, and appear to suffer no major health deficits as a consequence of their disorder, despite sometimes quite high (110–114 g/daily) levels of glucose excreted. The major symptoms evident in these patients include polyphagia, polyuria and polydipsia, and the kidneys appear to be normal in structure and function. Thus, from the evidence available thus far, defects in renal reuptake of glucose appear to have minimal long term negative consequences in otherwise normal individuals.

The following references disclose O-aryl glucosides SGLT2 inhibitors for treating diabetes.

EP 598359A1 (also JP 035988) (Tanabe Seiyaku) discloses compounds of the following structure A

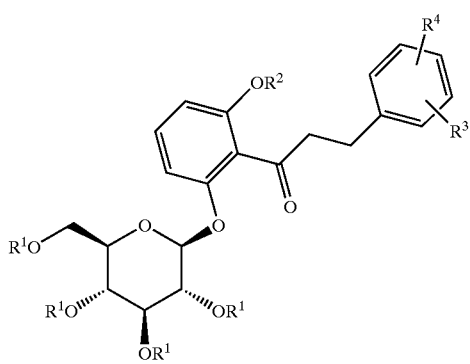

$R^1$ = H, acyl,
$R^2$ = H, Me
$R^3$, $R^4$ can be a variety of substituents

EP 0850948A1 discloses structures of the following genus B

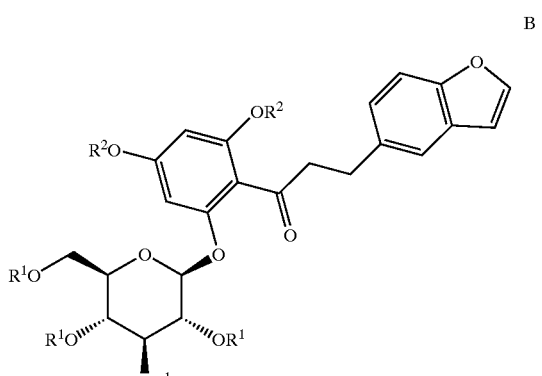

$R^1$ = H, acyl, CO(OAlkyl)
$R^2$ = H, allyl
$R^3$ = H or Me

JP 09188625A expands upon structure B to include examples of B where $R^3$ is H and where the 5 membered ring is saturated as well as the counterparts of benzothiophenes (O=S) and indenes (O=CH$_2$).

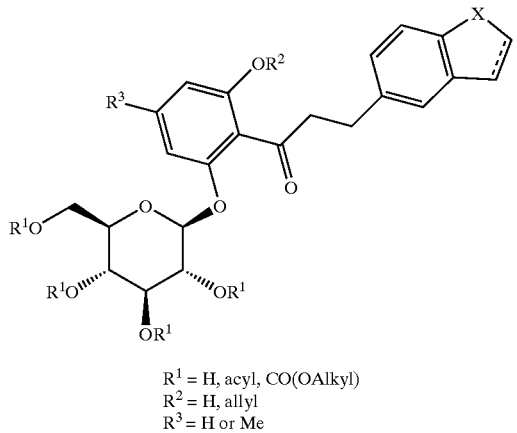

$R^1$ = H, acyl, CO(OAlkyl)
$R^2$ = H, allyl
$R^3$ = H or Me

JP 09124685A expands upon structure B for $R^3$=H to include derivatives of mono acylated C6 hydroxyl where the acyl group is a substituted benzoic or pyridyl carboxylic acid or a urethane generated from the corresponding phenol.

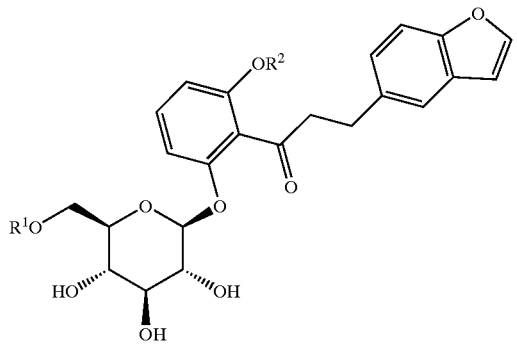

$R^1$ = H, acylaryl, CO(OAryl)
$R^2$ = H

JP 09124684 discloses derivatives of structure B

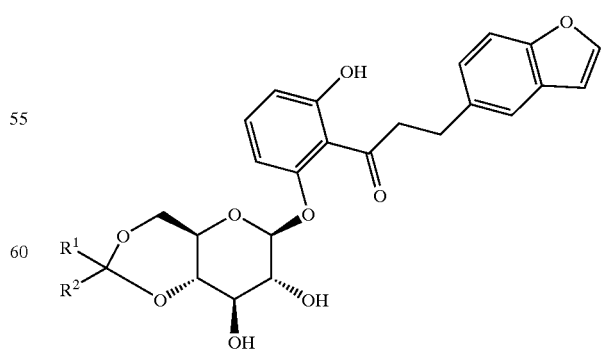

$R^1$, $R^2$ = H, alkyl, alkoxy, aryl or together oxo

EP 773226-A1 discloses derivatives of structure B

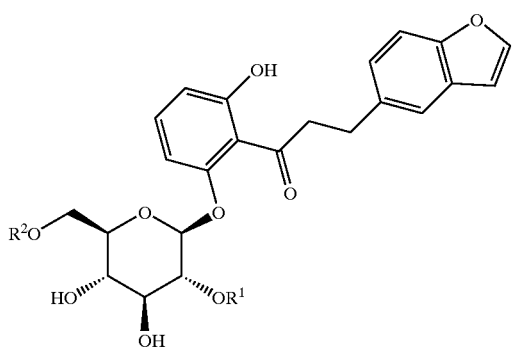

R¹ = alkanoyl if R² = H
R² = alkoxycarbonyl if R¹ = H

JP 08027006-A discloses derivatives of structure A where various combinations of the glucose hydroxyl are acylated and appears to be similar to EP 598359A1

EP 684254-A1 appears to encompass derivatives of structure B disclosed in JP 09188625A.

Other disclosures and publications which disclose SGLT2 inhibitors include the following:

K. Tsujihara et al, *Chem. Pharm. Bull.* 44, 1174–1180 (1996)

M. Hongu et al, *Chem. Pharm. Bull.* 46, 22–33 (1998)

M. Hongu et al, *Chem. Pharm. Bull.* 46, 1545–1555 (1998)

A. Oku et al, *Diabetes,* 48, 1794–1800 (1999)

JP 10245391 (Dainippon) discloses 500 structures as hypoglycemic agents for treatment of diabetes. These are O-glucosides of hydroxylated coumarins.

WO 98/31697 discloses compounds of the structure

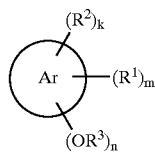

Where Ar includes, among others, phenyl, biphenyl, diphenylmethane, diphenylethane, and diphenylether, and R¹ is a glycoside, R² is H, OH, amino, halogen, carboxy, alkyl, cycloalkyl, or carboxamido, and R³ is hydrogen, alkyl, or acyl, and k, m, and n are independently 1–4. A subset of compounds disclosed in WO 98/31697 contains compounds of the following structures

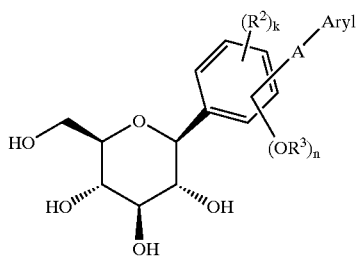

A is O or $(CH_2)_x$ where x = 0–3
$R^3$ is hydrogen, alkyl or acyl group where n is 1–4
$R^2$ is hydrogen, alkyl, OH, $NH_2$, halogen, $CO_2H$ or carboximide where k is 1–4 which are disclosed for use in the treatment or prevention of inflammatory diseases, autoimmune diseases, infections, cancer, and cancer metastasis, reperfusion disorders, thrombosis, ulcer, wounds, osteoporosis, diabetes mellitus and atherosclerosis, among others.

DESCRIPTION OF THE INVENTION

In accordance with the present invention, C-aryl glucoside compounds are provided which have the structure I

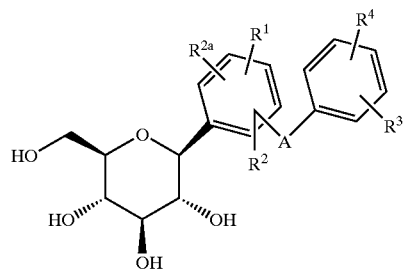

wherein
$R^1$, $R^2$ and $R^{2a}$ are independently hydrogen, OH, $OR^5$, alkyl, $CF_3$, $OCHF_2$, $OCF_3$, $SR^{5i}$ or halogen, or two of $R^1$, $R^2$ and $R^{2a}$ together with the carbons to which they are attached can form an annelated five, six or seven membered carbocycle or heterocycle which may contain 1 to 4 heteroatoms in the ring which are N, O, S, SO, and/or $SO_2$;

$R^3$ and $R^4$ are independently hydrogen, OH, $OR^{5a}$, OAryl, $OCH_2$Aryl, alkyl, cycloalkyl, $CF_3$, —$OCHF_2$, —$OCF_3$, halogen, —CN, $CO_2R^{5b}$, —$CO_2H$, —$COR^{6b}$, —CH(OH) $R^{6c}$, —CH($OR^{5h}$)$R^{6d}$, —$CONR^6R^{6a}$, —$NHCOR^{5c}$, —$NHSO_2R^{5d}$, —$NHSO_2$Aryl, Aryl, —$SR^{5e}$, —$SOR^{5f}$, —$SO_2R^{5g}$, —$SO_2$Aryl, or a five, six or seven membered heterocycle which may contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which may contain 1 to 4 heteroatoms in the ring which are N, O, S, SO, and/or $SO_2$;

$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;

$R^6$, $R^{6a}$, $R^{6b}$, $R^{6c}$ and $R^{6d}$ are independently hydrogen, alkyl, aryl, alkylaryl or cycloalkyl, or $R^6$ and $R^{6a}$ together with the nitrogen to which they are attached form an annelated five, six or seven membered heterocycle which may contain 1 to 4 heteroatoms in the ring which are N, O, S, SO, and/or $SO_2$;

A is O, S, NH, or $(CH_2)_n$ where n is 0–3, and a pharmaceutically acceptable salt thereof, all stereoisomers thereof, and all prodrug esters thereof.

The compounds of formula I possess activity as inhibitors of the sodium dependent glucose transporters found in the intestine and kidney of mammals and are useful in the treatment of diabetes and the micro- and macrovascular complications of diabetes such as retinopathy, neuropathy, nephropathy, and wound healing.

The present invention provides, in particular, for methods of using such compounds.

Specifically, in accordance with the present invention, a method is provided for treating or delaying the progression or onset of diabetes, especially type I and type II diabetes, including complications of diabetes, including retinopathy, neuropathy, nephropathy and delayed wound healing, and related diseases such as insulin resistance (impaired glucose homeostasis), hyperglycemia, hyperinsulinemia, elevated blood levels of fatty acids or glycerol, obesity, hyperlipidemia including hypertriglyceridemia, Syndrome X, atherosclerosis and hypertension, and for increasing high density lipoprotein levels, wherein a therapeutically effective amount of a compound of structure I is administered to a human patient in need of treatment.

In addition, in accordance with the present invention, a method is provided for treating diabetes and related diseases as defined above and hereinafter, wherein a therapeutically effective amount of a combination of a compound of structure I and another type of antidiabetic agent and/or another type of therapeutic agent such as a hypolipidemic agent is administered to a human patient in need of treatment.

The conditions, diseases, and maladies collectively referred to as "Syndrome X" (also known as Metabolic Syndrome) are detailed in Johannsson *J. Clin. Endocrinol. Metab.*, 82, 727–34 (1997).

The term "other type of therapeutic agents" as employed herein refers to one or more antidiabetic agents (other than SGLT2 inhibitors of formula I), one or more anti-obesity agents, anti-hypertensive agents, anti-platelet agents, anti-atherosclerotic agents and/or one or more lipid-lowering agents (including anti-atherosclerosis agents).

In the above method of the invention, the compound of structure I of the invention will be employed in a weight ratio to the one, two or more antidiabetic agent and/or one, two or more other type therapeutic agent (depending upon its mode of operation) within the range from about 0.01:1 to about 300:1, preferably from about 0.1:1 to about 10:1.

Preferred is the use of compounds of formula IA

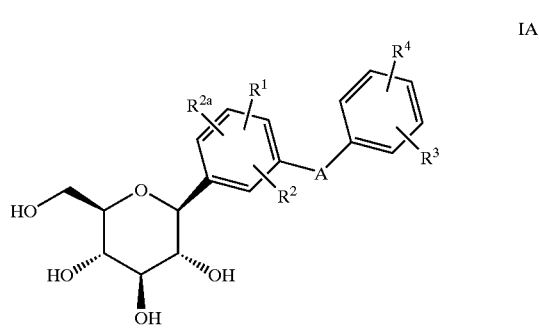

IA wherein A is $CH_2$ or O or S and is linked meta to the glucoside;

$R^1$, $R^2$ and $R^{2a}$ are independently selected from H, lower alkyl, halogen, $OR^5$, or $OCHF_2$ or two of $R^1$, $R^2$ and $R^{2a}$ are H and the other is lower alkyl, halogen, $OR^5$ or $OCHF_2$;

$R^3$ and $R^4$ are independently selected from lower alkyl, $OR^{5a}$, —$OCHF_2$, —$SR^{5e}$, OH, —$CO_2R^{5b}$, -3,4-($OCH_2O$)—, —$COR^{6b}$, —$CH(OH)R^{6c}$, —$CH(OR^{5h})R^{6d}$, $CF_3$,

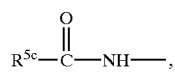

—$SOR^{5f}$, —$SO_2R^{5g}$, aryl, —$NHSO_2$Aryl, —$NHSO_2R^{5d}$, COOH, thiadiazole, tetrazole, —$OCH_2$Aryl, —$OCF_3$, OAryl, or H.

More preferred is the use of compounds of formula I where A is $CH_2$;
$R^1$ is hydrogen, halogen or lower alkyl;
$R^2$ and $R^{2a}$ are each H;
$R^3$ is H;
$R^4$ is lower alkyl, —$COR^{6b}$, —$CH(OH)R^{6c}$, —$CH(OR^{5h})$ $R^{6d}$, $R^{5a}O$, —$OCHF_2$, —$OCF_3$ or —$SR^{5e}$.

Most preferred is the use of compounds of formula I of the structure IB

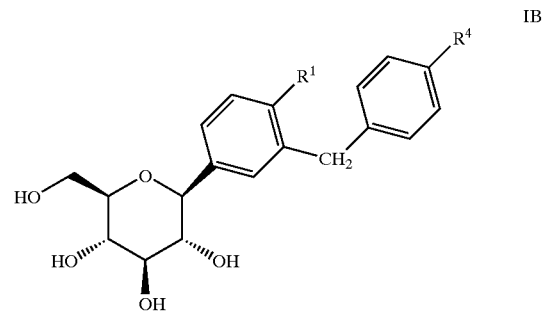

IB where $R^1$ is hydrogen, halogen or lower alkyl and $R^4$ is lower alkyl, $R^{5a}O$, —$OCHF_2$, or —$SR^{5e}$. It is preferred that $R^1$ be linked para to the glucoside bond and the $R^4$ substituent be linked at the para position.

DETAILED DESCRIPTION OF THE INVENTION

The compounds of formula I can be prepared as shown in the following reaction schemes and depscription thereof wherein temperatures are expressed in degrees Centigrade.

Compounds of formula I can be prepared as shown in Scheme 1 by treatment of compounds of formula II

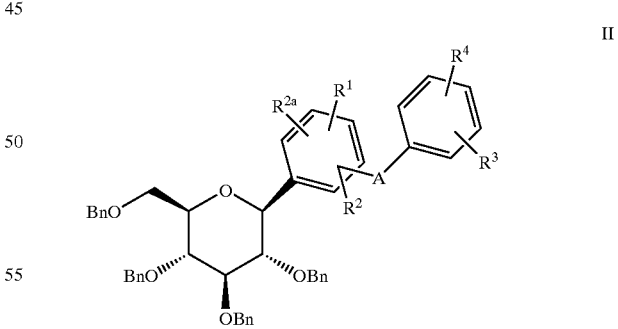

II (where Bn=benzyl) with $H_2$ in the presence of a catalyst such as 1) Pd/C employing a solvent such as MeOH or EtOH or 2) preferably Pd(OH)$_2$ using a solvent such as EtOAc. Alternatively, compounds of formula I can be prepared by treatment of compounds of formula II with a Lewis acid such BBr$_3$, BCl$_3$, or BCl$_3$·Me$_2$S in a solvent such as $CH_2Cl_2$ at −78°. Compounds of formula I can also be prepared by treatment of compounds of formula II in a solvent such as EtSH containing BF$_3$·Et$_2$O, at 20°.

Compounds of formula II can be prepared by treatment of compounds of formula III with silanes such as Et₃SiH or preferably (iPr)₃SiH in a solvent such as MeCN or mixtures of MeCN/CH₂Cl₂ containing a Lewis acid such as BF₃·Et₂O at −30°.

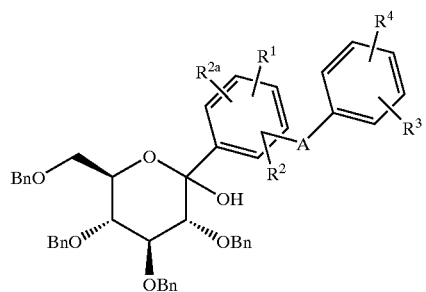

III

Compounds of formula III can be prepared by coupling of a compound of formula IV

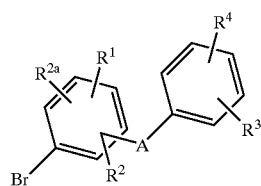

IV with compound V.

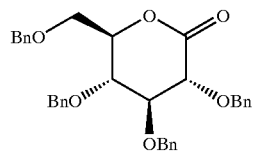

V

Compounds of formula IV are activated for coupling by treatment with n-BuLi or t-BuLi at −78° in a solvent such as THF prior to addition of lactone V. Preparation of lactone V is described in. R. Benhaddou, S Czernecki, et al., *Carbohydr. Res.*, 260 (1994), 243–250.

Scheme 1

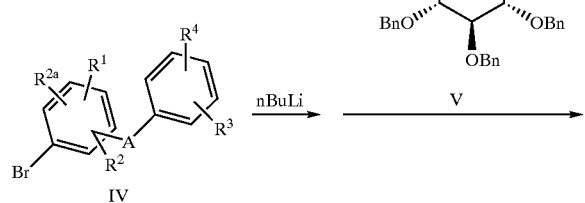

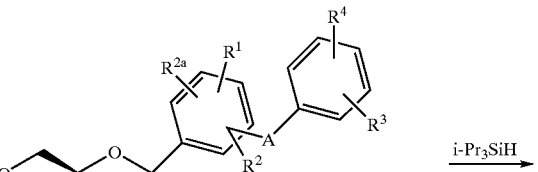

III

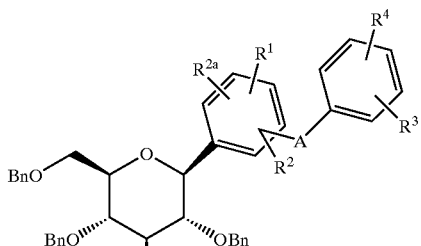

II

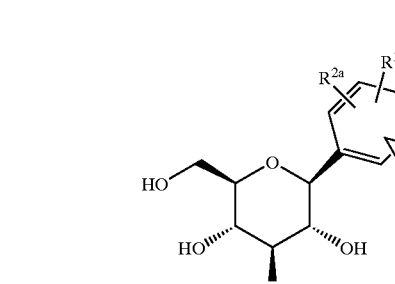

I

Compounds of formula IV where A is $(CH_2)_n$ where n=1–3 can be prepared as shown in Scheme 2 by treatment of compounds of formula VI

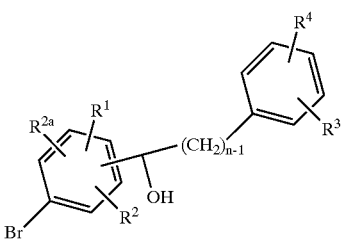

VI with silanes such as Et₃SiH in a solvent such as MeCN or CH₂Cl₂ containing a Lewis acid such as BF₃·Et₂O or TFA at −30° to +60°.

Compounds of formula VI can be prepared by coupling commercially available bromobenzaldehydes of formula VII

VII

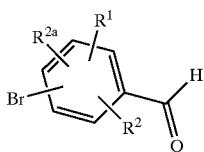

with either the lithium or magnesium organometalic derivative of compounds of formula VIII

VIII

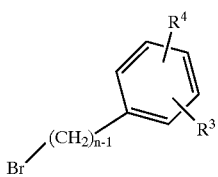

in a solvent such as $Et_2O$ or THF using conditions familiar to those skilled in the art.

Compounds of formula VIII are either commercially available or readily prepared by standard methods known to those skilled in the art.

Scheme 2

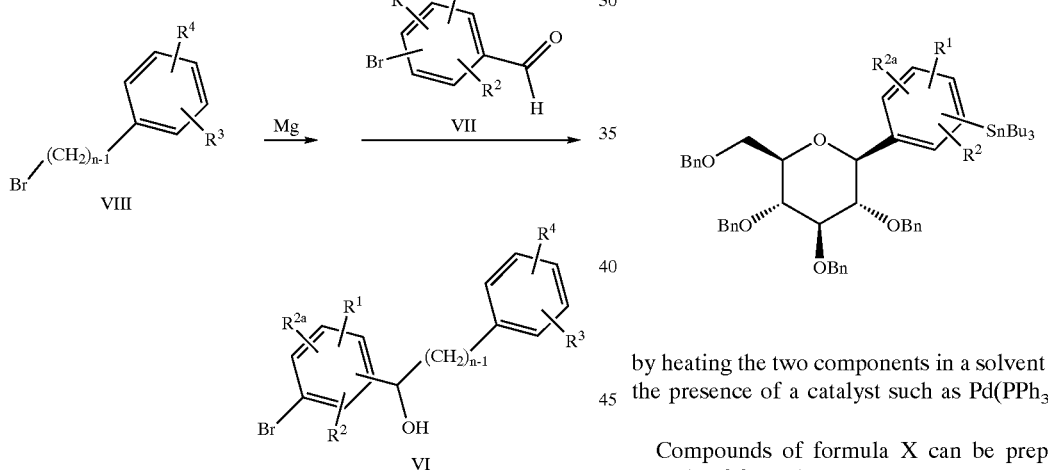

Compounds of formula I where $R^4$ is $CH(OR^{5h})R^{6d}$ can be prepared by treatment of compounds of formula I where $R^4$ is $COR^{6b}$ sequentially with 1) an acetylating agent such as $Ac_2O$ in a solvent such as pyridine alone or $CH_2Cl_2$ containing 1.5 equivalents of a base such as $Et_3N$, 2) a reducing agent such as $NaBH_4$ in a solvent such as EtOH, 3) an alkylating agent such as $R^{5h}Br$ or $R^{5h}I$ in the presence of a base such as NAH in a solvent such as DMF, and 4) alkaline ester hydrolysis conditions such as LiOH in a 2:3:1 mixture of $THF/MeOH/H_2O$.

Compounds of formula I where $R^4$ is $CH(OH)R^{6c}$ can be prepared by treatment of compounds of formula I where $R^4$ is $COR^{6b}$ with a reducing agent such as $NaBH_4$ in a solvent such as EtOH.

Compounds of formula I where $R^4$ is $COR^{6b}$ can be prepared by treatment of compounds of formula II where $R^4$ is $COR^{6b}$ with a Lewis acid such as $BCl_3$ or $BBr_3$ at $-78°$ in a solvent such as $CH_2Cl_2$.

Compounds of formula II where A is $CH_2$ and $R^4$ is $-COR^{6b}$ can be prepared as shown in Scheme 3 by coupling commercially available or readily accessible compounds of formula IX

IX

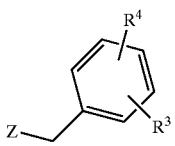

where Z is Br or Cl with compounds of formula X

X

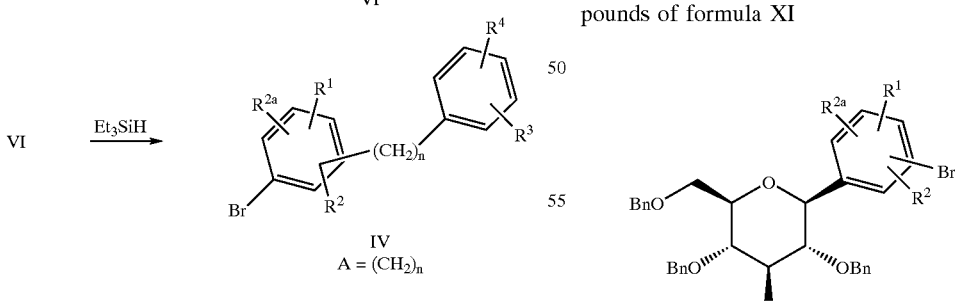

by heating the two components in a solvent such as PhMe in the presence of a catalyst such as $Pd(PPh_3)_4$.

Compounds of formula X can be prepared from compounds of formula XI

XI by treatment with $(Bu_3Sn)_2$ and a catalyst such as $Pd(Ph_3P)_4$ in a solvent such as toluene.

Compounds of formula XI can be prepared from compounds of formula XII

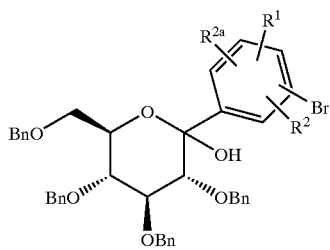

XII by treatment with silanes such as iPr$_3$SiH or Et$_3$SiH in a solvent such as MeCN containing a Lewis acid such as BF$_3$·Et$_2$O at −30°.

Compounds of formula XII can be prepared by coupling compound V with the organolithium obtained upon treatment of compounds of formula XIII

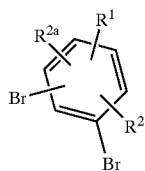

XIII with n-BuLi or t-BuLi at −78° in THF.

Scheme 3

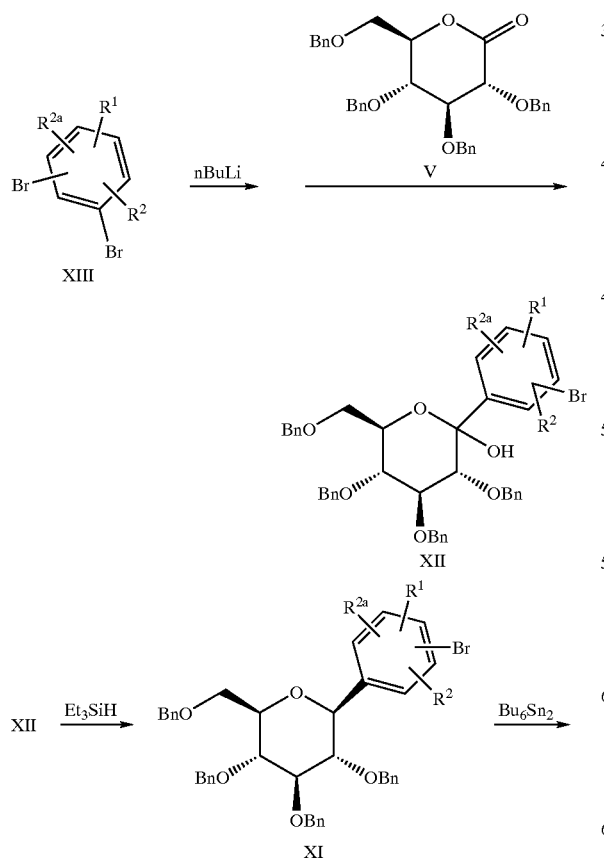

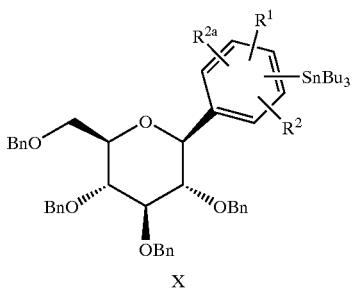

X

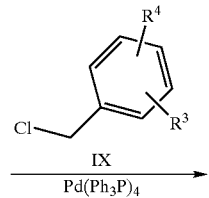

IX $\xrightarrow{\text{Pd(Ph}_3\text{P)}_4}$

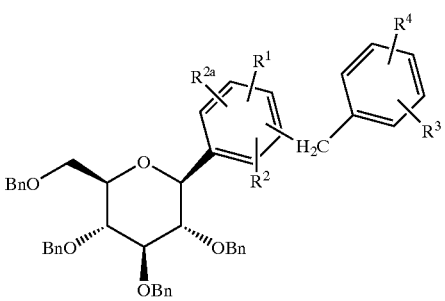

II

An alternative synthesis (Scheme 4) of compounds of formula IV where A is CH$_2$ entails reduction of compounds of formula XIV

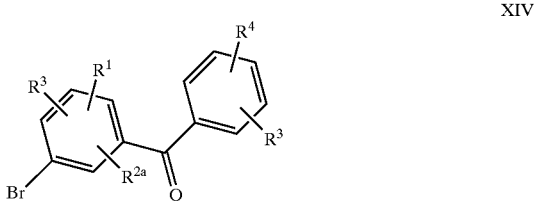

XIV with a reducing agent such as Et$_3$SiH in a solvent such as MeCN or CH$_2$Cl$_2$ or mixtures thereof containing a catalyst such as BF$_3$·Et$_2$O.

Compounds of formula XIV can be readily prepared by Friedel-Craft acylation of commercially available hydrocarbons of formula XV

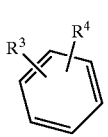

XV with readily available acid chlorides of formula XVI

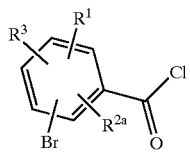
XVI in a solvent such as $CS_2$ containing two equivalents of a Lewis Acid such as $AlCl_3$ or $AlBr_3$.

Scheme 4

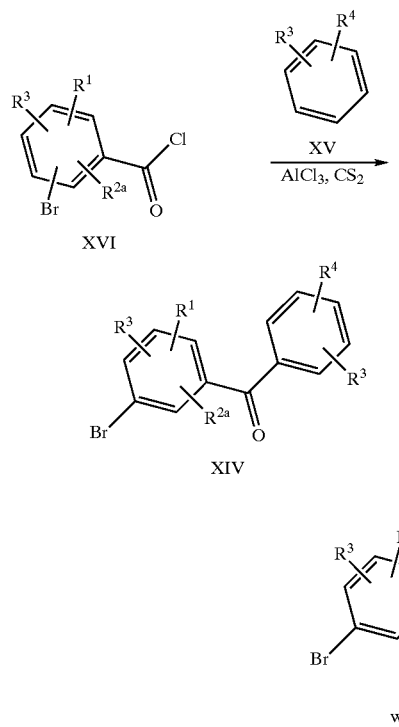

Compounds of formula II where A is a bond can be prepared as shown in Scheme 5 by coupling compounds of formula XI with compounds of formula XVII

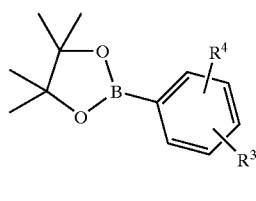
XVII or the corresponding boronic acid XVIII.

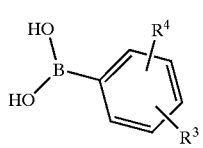
XVIII

Coupling entails heating in the presence of a catalyst such as $Pd(PPh_3)_4$ employing a solvent such as 3:1 PhMe/EtOH containing $Na_2CO_3$. Compounds of formula XVIII are either commercially available or can be prepared upon treatment of compounds of formula XVII with $BCl_3$ in a solvent such as $CH_2Cl_2$. Compounds of formula XVII can be prepared by heating compounds of formula XIX

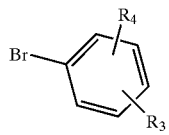
XIX in a solvent such as DMSO containing a catalyst such as $PdCl_2 \cdot dppf$ and a base such as KOAc with compound XX.

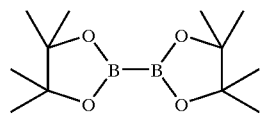
XX

Scheme 5

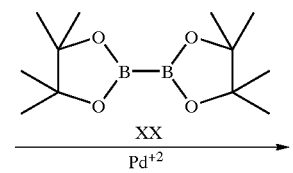

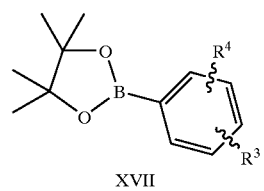
XVII

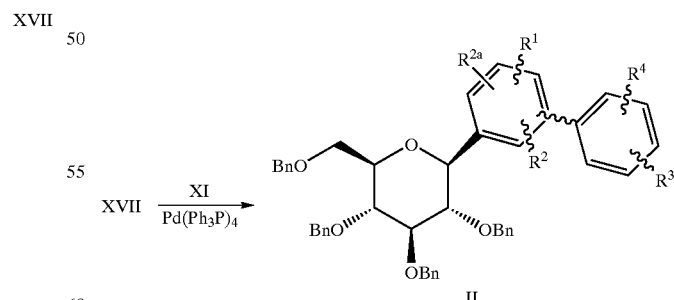

Compounds of formula II, where $A=CH_2$ and $R^2=OH$, can be prepared as shown in Scheme 6 upon sequential treatment of compounds of formula XXI

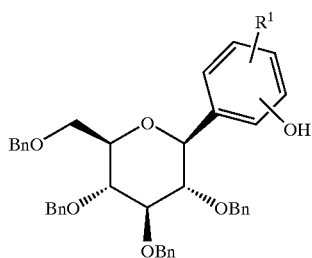

XXI with a base such as NaH followed by heating with compounds of formula IX in a solvent such as PhMe.

Compounds of formula XXI can be prepared from compounds of formula XXII

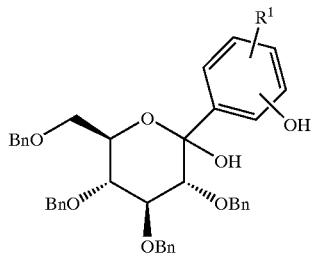

XXII by treatment with silanes such as Et$_3$SiH or i-Pr$_3$SiH in a solvent such as MeCN containing a Lewis acid such as BF$_3$.Et$_2$O at −30°.

Compounds of formula XXII can be prepared by coupling the compound of formula V with activated metallated derivatives of compounds of formula XXIII

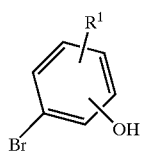

which are prepared by sequential treatment of XXIII with a base such as NaH, KH, or KOtBu followed by an alkyllithium such as nBuLi or tBuLi in a solvent such as dry THF.

Scheme 6

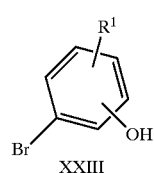
XXIII
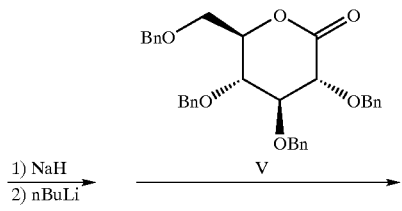
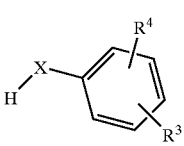

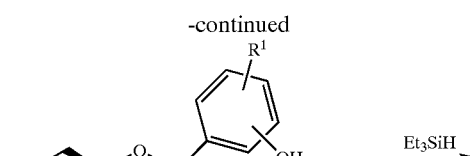

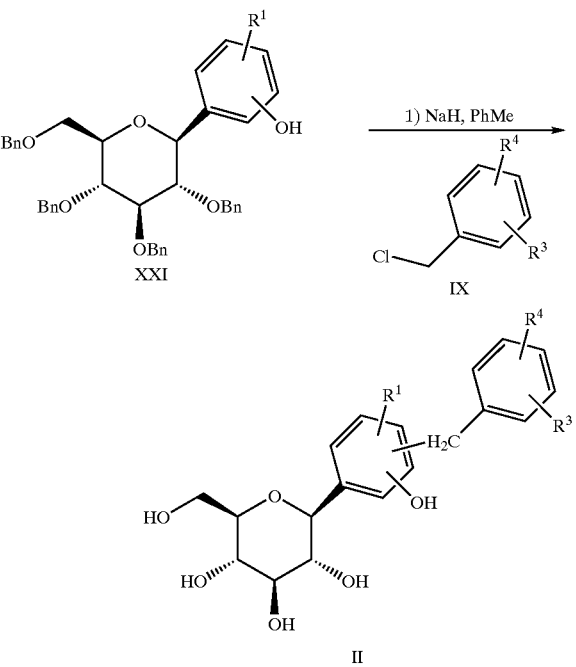

Compounds of formula I, where A=O or NH, can be prepared as shown in Scheme 7 by coupling compounds of formula XXIV

XXIV

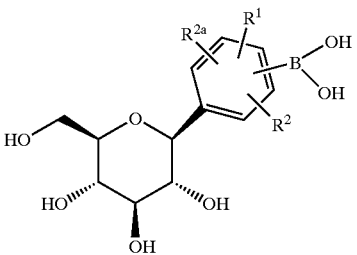

with commercially available compounds of formula XXV where X=O or NH

XXV by heating in a solvent such as pyridine containing a base such as Et$_3$N, a catalyst such as Cu(OAc)$_2$ and molecular sieves.

Compounds of formula XXIV can be prepared by treating compounds of formula XXVI with BCl₃ in a solvent such as CH₂Cl₂ at −78°.

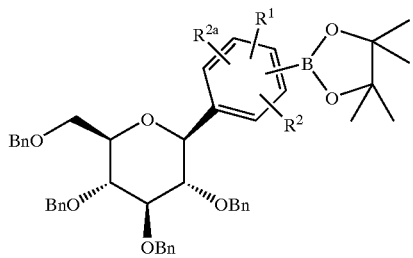

XXVI

Compounds of formula XXVI can be prepared by heating compounds of formula XI with compounds of formula XX in a solvent such as DMSO containing a catalyst such as PdCl₂·dppf and a base such as KOAc.

Scheme 7

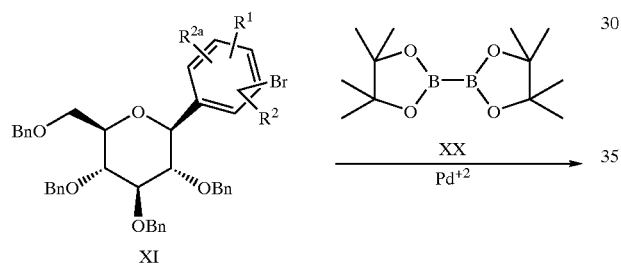

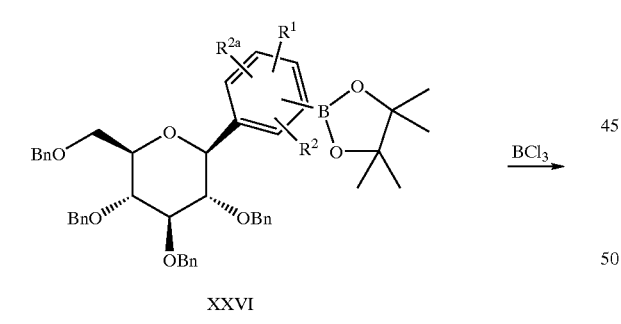

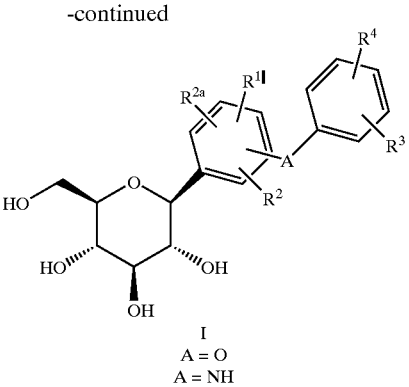

I
A = O
A = NH

Compounds of formula IV where A is O or NH can be prepared as shown in Scheme 8 by coupling compounds of formula XVIII

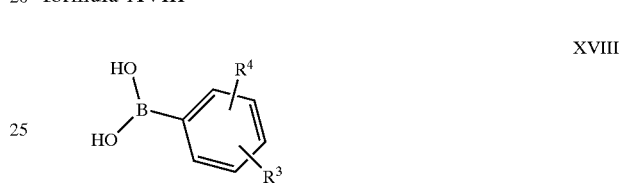

XVIII with compounds of formula XXVII where X=O or NH

XXVII by heating in a solvent such as pyridine containing a base such as Et₃N, a catalyst such as Cu(OAc)₂ and molecular sieves.

Scheme 8

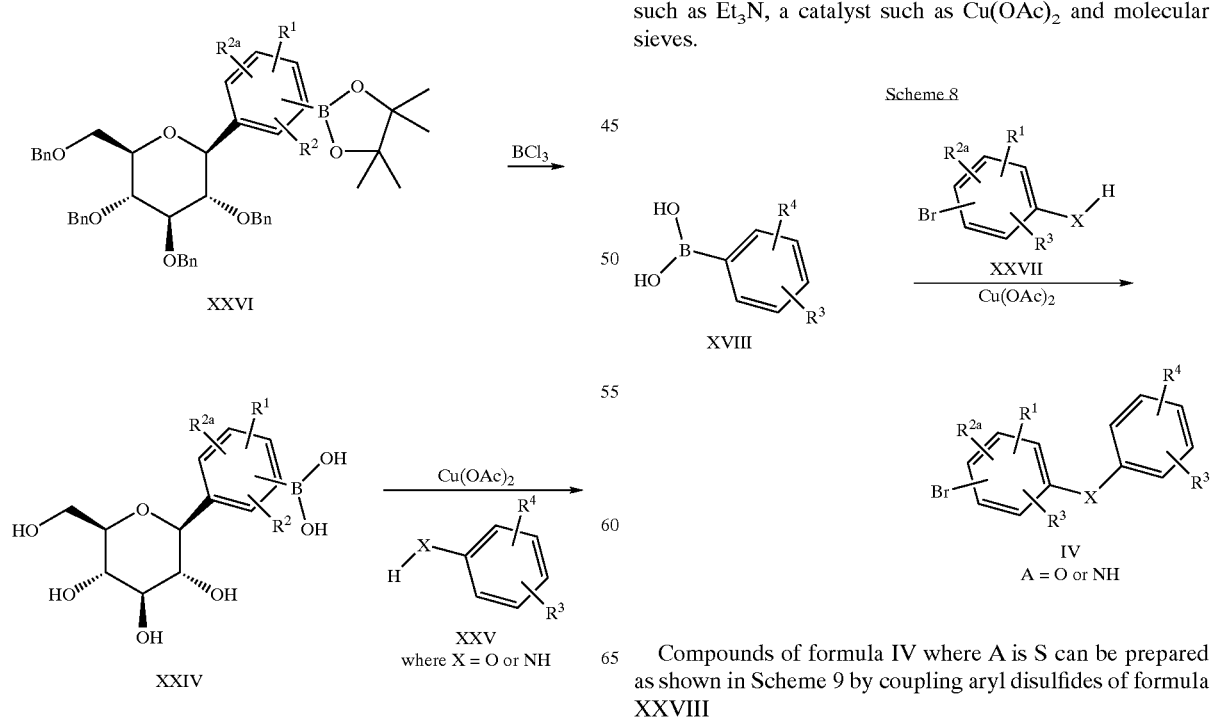

IV
A = O or NH

Compounds of formula IV where A is S can be prepared as shown in Scheme 9 by coupling aryl disulfides of formula XXVIII

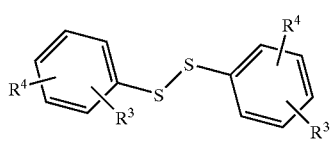

XXVIII with the organolithium obtained upon metalation of compounds of formula XIII with n-BuLi or t-BuLi at −78° in THF.

Scheme 9

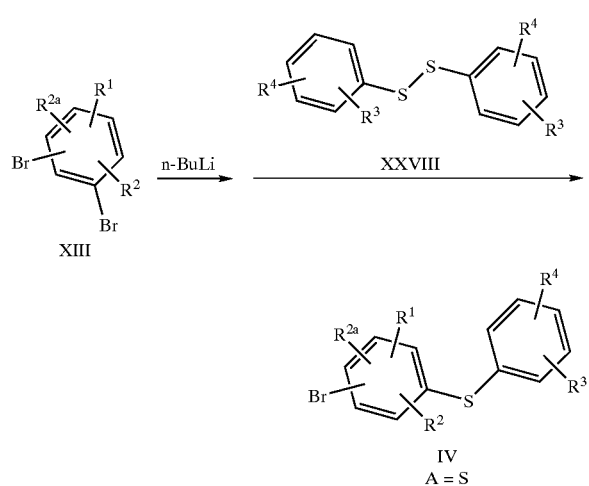

Listed below are definitions of various terms used in the description of the instant invention. These definitions apply to the terms as they are used throughout the specification (unless they are otherwise limited in specific instances) either individually or as part of a larger group.
The following abbreviations are employed herein:
Ph=phenyl
Bn=benzyl
t-Bu=tertiary butyl
Me=methyl
Et=ethyl
TMS=trimethylsilyl
$TMSN_3$=trimethylsilyl azide
TBS=tert-butyldimethylsilyl
THF=tetrahydrofuran
$Et_2O$=diethyl ether
EtOAc=ethyl acetate
DMF=dimethyl formamide
MeOH=methanol
EtOH=ethanol
i-PrOH=isopropanol
HOAc or AcOH=acetic acid
TFA=trifluoroacetic acid
i-$Pr_2$NEt=diisopropylethylamine
$Et_3$N=triethylamine
DMAP=4-dimethylaminopyridine
$NaBH_4$=sodium borohydride
$LiAlH_4$=lithium aluminum hydride
n-BuLi=n-butyllithium
Pd/C=palladium on carbon
KOH=potassium hydroxide
NaOH=sodium hydroxide
LiOH=lithium hydroxide
$K_2CO_3$=potassium carbonate
$NaHCO_3$=sodium bicarbonate
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.$H_2O$=1-hydroxybenzotriazole hydrate
HOAT=1-Hydroxy-7-azabenzotriazole
$Ph_3P$=triphenylphosphine
$Pd(OAc)_2$=Palladium acetate
$(Ph_3P)_4Pd^0$=tetrakis triphenylphosphine palladium
Ar=argon
$N_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS high performance liquid chromatography/mass spectrometry
MS or Mass Spec=mass spectrometry
NMR=nuclear magnetic resonance
mp=melting point
dppf=diphenylphosphinoferrocene Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

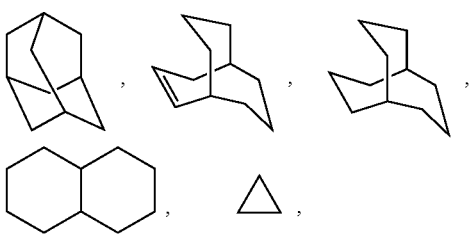
, any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the alkyl substituents.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "alkanoyl" as used herein alone or as part of another group refers to alkyl linked to a carbonyl group.

Unless otherwise indicated, the term "lower alkenyl" as used herein by itself or as part of another group refers to straight or branched chain radicals of 2 to 8 carbons, and the term "alkenyl" as used herein by itself or as part of another group refers to straight or branched chain radicals of 2 to 20 carbons, preferably 2 to 12 carbons, and more preferably 2 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the alkyl substituents set out herein.

Unless otherwise indicated, the term "lower alkynyl" as used herein by itself or as part of another group refers to straight or branched chain radicals of 2 to 8 carbons, and the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

The terms "arylakyl", "arylalkenyl" and "arylalkynyl" as used alone or as part of another group refer to alkyl, alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

Suitable alkylene, alkenylene or alkynylene groups $(CH_2)_m$ or $(CH_2)_p$ (where p is 1 to 8, preferably 1 to 5, and m is 1 to 5, preferably 1 to 3, which includes alkylene, alkenylene or alkynylene groups) as defined herein, may optionally include 1, 2, or 3 substituents which include alkyl, alkenyl, halogen, cyano, hydroxy, alkoxy, amino, thioalkyl, keto, $C_3$-$C_6$ cycloalkyl, alkylcarbonylamino or alkylcarbonyloxy.

Examples of $(CH_2)_m$ or $(CH_2)_p$, alkylene, alkenylene and alkynylene include —$CH_2$—, —$CH_2CH_2$—,

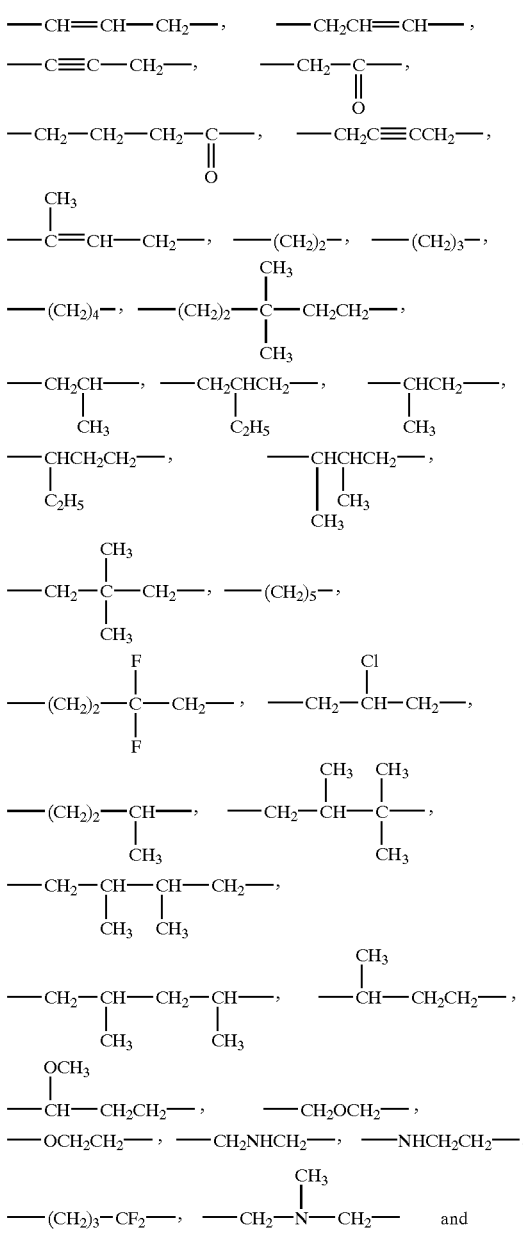

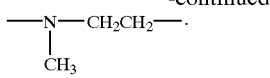

The term "halogen" or "halo" as used herein alone or as part of another group refers to chlorine, bromine, fluorine, and iodine, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or "Aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

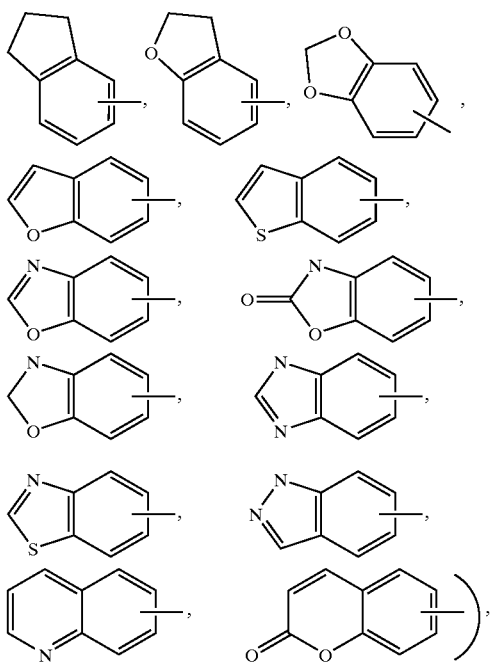

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl and thioalkyl. These substituents may be further substituted with a carboxylic acid and/or any of the alkyl substituents as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or as part of another group, as defined herein, refers to an organic radical linked to a carbonyl

group; examples of acyl groups include any of the alkyl substituents attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 1, 2 or 3), such as

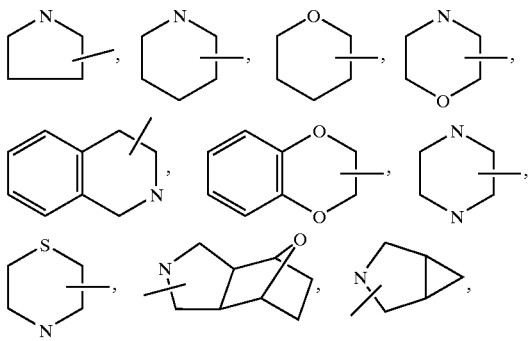

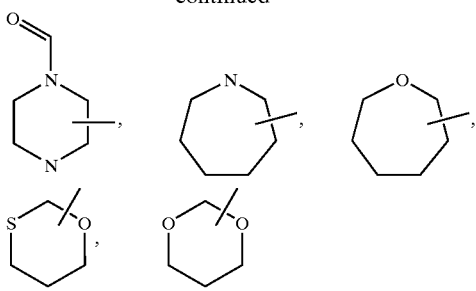

and the like. The above groups may include 1 to 4 substituents such as alkyl, halo, oxo and/or any of the alkyl substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g., benzothiophenyl or indolyl), and includes possible N-oxides. The heteroaryl group may optionally include 1 to 4 substituents such as any of the the alkyl substituents set out above. Examples of heteroaryl groups include the following:

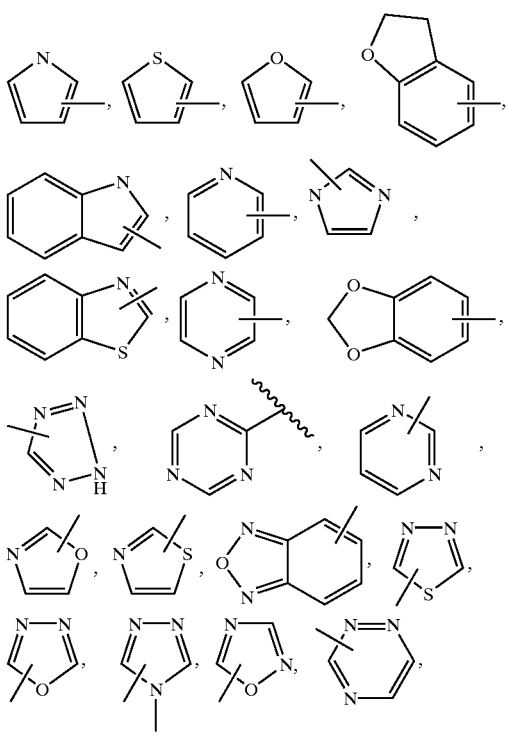

and the like.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a $-(CH_2)_p-$ chain, alkylene or alkenylene as defined above.

The term "five, six or seven membered carbocycle or heterocycle" as employed herein refers to cycloalkyl or cycloalkenyl groups as defined above or heteroaryl groups or cycloheteroaryl groups as defined above, such as thiadiazaole, tetrazole, imidazole, or oxazole.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like. In addition, prodrug esters which are known in the art for carboxylic and phosphorus acid esters such as methyl, ethyl, benzyl and the like.

Examples of such prodrug esters include

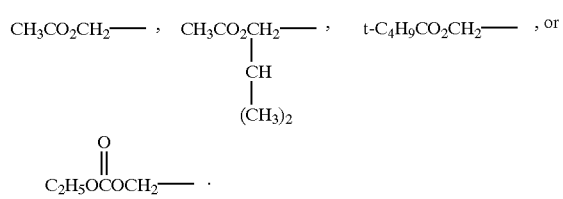

Where the compounds of structure I are in acid form they may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, lysine (D or L), ethylenediamine, t-butylamine, t-octylamine, tris-(hydroxymethyl) aminomethane (TRIS), N-methyl glucosamine (NMG), triethanolamine and dehydroabietylamine.

All stereoisomers of the compounds used in the instant invention are contemplated, either in admixture or in pure or substantially pure form. The compounds used in the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Where desired, the compounds of structure I may be used in combination with one or more other types of antidiabetic agents and/or one or more other types of therapeutic agents which may be administered orally in the same dosage form, in a separate oral dosage form or by injection.

The other type of antidiabetic agent which may be optionally employed in combination with the SGLT2 inhibitor of formula I may be 1,2,3 or more antidiabetic agents or antihyperglycemic agents including insulin secretagogues or insulin sensitizers, or other antidiabetic agents preferably having a mechanism of action different from SGLT2 inhibition and may include biguanides, sulfonyl ureas, glucosidase inhibitors, PPAR γ agonists such as thiazolidinediones, aP2 inhibitors, PPAR α/γ dual agonists, dipeptidyl peptidase IV (DP4) inhibitors, and/or meglitinides, as well as insulin, glucagon-like peptide-1 (GLP-1), PTP1B inhibitors, glycogen phosphorylase inhibitors and/or glucos-6-phosphatase inhibitors.

The other types of therapeutic agents which may be optionally employed in combination with the SGLT2 inhibitors of formula I include anti-obesity agents, antihypertensive agents, antiplatelet agents, antiatherosclerotic agents and/or lipid lowering agents.

The SGLT2 inhibitors of formula I may also be optionally employed in combination with agents for treating complications of diabetes. These agents include PKC inhibitors and/or AGE inhibitors.

It is believed that the use of the compounds of structure I in combination with 1, 2, 3 or more other antidiabetic agents produces antihyperglycemic results greater than that possible from each of these medicaments alone and greater than the combined additive antihyperglycemic effects produced by these medicaments.

The other antidiabetic agent may be an oral antihyperglycemic agent preferably a biguanide such as metformin or phenformin or salts thereof, preferably metformin HCl.

Where the other antidiabetic agent is a biguanide, the compounds of structure I will be employed in a weight ratio to biguanide within the range from about 0.01:1 to about 100:1, preferably from about 0.1:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.2:1 to about 10:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.5:1 to about 50:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.2:1 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with an antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (Amylen) and LY-315902 (Lilly), which may be administered via injection, intranasal, or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. provisional application No. 60/155,400, filed Sep. 22, 1999, the disclosure of which is incorporated herein by reference, employing dosages as set out therein, which compounds designated as preferred are preferred for use herein.

The other antidiabetic agent may be an aP2 inhibitor such as disclosed in U.S. application Ser. No. 09/391,053, filed Sep. 7, 1999, and in U.S. provisional application No. 60/127,745, filed Apr. 5, 1999, employing dosages as set out herein. Preferred are the compounds designated as preferred in the above application.

The other antidiabetic agent may be a DP4 inhibitor such as disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The SGLT2 inhibitor of formula I will be employed in a weight ratio to the meglitinide, PPAR γ agonist, PPAR α/γ dual agonist, aP2 inhibitor or DP4 inhibitor within the range from about 0.01:1 to about 100:1, preferably from about 0.2:1 to about 10:1.

The hypolipidemic agent or lipid-lowering agent which may be optionally employed in combination with the compounds of formula I of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications. All of the above U.S. Patents and applications are incorporated herein by reference.

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. The hypolipidemic agent may also be the compounds disclosed in U.S. provisional application Nos. 60/211,594 and 60/211,595. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, atavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl]pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

Preferred hypolipidemic agents are pravastatin, lovastatin, simvastatin, atorvastatin, fluvastatin, cerivastatin, atavastatin and rosuvastatin.

The above-mentioned U.S. patents are incorporated herein by reference. The amounts and dosages employed will be as indicated in the Physician's Desk Reference and/or in the patents set out above.

The compounds of formula I will be employed in a weight ratio to the hypolipidemic agent (where present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for is example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The other hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties, Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agents are pravastatin, simvastatin, lovastatin, atorvastatin, fluvastatin, cerivastatin, atavastatin and rosuvastatin.

When the other type of therapeutic agent which may be optionally employed with the SGLT2 inhibitor of formula I is 1, 2, 3 or more of an anti-obesity agent, it may include a beta 3 adrenergic agonist, a lipase inhibitor, a serotonin (and dopamine) reuptake inhibitor, a thyroid receptor beta drug, an anorectic agent, an NPY antagonist, a Leptin analog and/or an MC4 agonist.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor beta compound which may be optionally employed in combination with a compound of formula I may be a thyroid receptor ligand as disclosed in WO97/21993 (U. Cal SF), WO99/00353 (KaroBio) and GB98/284425 (KaroBio), with compounds of the KaroBio applications being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

Examples of the anti-platelet agent(s) which may be optionally employed in combinations of this invention include abciximab, ticlopidine, eptifibatide, dipyridamole, aspirin, anagrelide, tirofiban and/or clopidogrel.

Examples of the anti-hypertensive agent(s) which may be optionally employed in combinations of this invention include ACE inhibitors, calcium antagonists, alpha-blockers, diuretics, centrally acting agents, angiotensin-II antagonists, beta-blockers and vasopeptidase inhibitors.

Examples of ACE inhibitors include lisinopril, enalapril, quinapril, benazepril, fosinopril, ramipril, captopril, enalaprilat, moexipril, trandolapril and perindopril; examples of calcium antagonists include amlodipine, diltiazem, nifedipine, verapamil, felodipine, nisoldipine, isradipine and nicardipine; examples of alpha-blockers include terazosin, doxazosin and prazosin; examples of diuretics include hydrochlorothiazide, torasemide, furosemide, spironolactone and indapamide; examples of centrally acting agents include clonidine and guanfacine; examples of angiotensin-II antagonists include losartan, valsartan, irbesartan, candesartan and telmisartan; examples of beta-blockers include metoprolol, propranolol, atenolol, carvedilol and sotalol; and examples of vasopeptidase inhibitors include omapatrilat and gemopatrilat.

In carrying out the method of the invention, a pharmaceutical composition will be employed containing the compounds of structure I, with or without another antidiabetic agent and/or antihyperlipidemic agent, or other type therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations, or they can be administered intranasally or in transdermal patches. The dose for adults is preferably between 10 and 2,000 mg per day, which can be administered in a single dose or in the form of individual doses from 1–4 times per day.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

SGLT2 inhibitor activity of the compounds of the invention may be determined by use of an assay system as set out below.

Assay for SGLT2 Activity

The mRNA sequence for human SGLT2 (GenBank #M95549) was cloned by reverse-transcription and amplification from human kidney mRNA, using standard molecular biology techniques. The cDNA sequence was stably transfected into CHO cells, and clones were assayed for SGLT2 activity essentially as described in Ryan et al. (1994). Evaluation of inhibition of SGLT2 activity in a clonally selected cell line was performed essentially as described in Ryan et al., with the following modifications. Cells were grown in 96-well plates for 2–4 days to 75,000 or 30,000 cells per well in F-12 nutrient mixture (Ham's F-12), 10% fetal bovine serum, 300 ug/ml Geneticin and penicillin-streptomycin. At confluence, cells were washed twice with 10 mM Hepes/Tris, pH 7.4, 137 mM N-methyl-D-glucamine, 5.4 mM KCl, 2.8 mM CaCl$_2$, 1.2 mM MgSO$_4$. Cells then were incubated with 10 µM [$^{14}$C]AMG, and 10 µM inhibitor (final DMSO=0.5%) in 10 mM Hepes/Tris, pH 7.4, 137 mM NaCl, 5.4 mM KCl, 2.8 mM CaCl$_2$, 1.2 mM MgSO$_4$ at 37° C. for 1.5 hr. Uptake assays were quenched with ice cold 1×PBS containing 0.5 mM phlorizin, and cells were then lysed with 0.1% NaOH. After addition of MicroScint scintillation fluid, the cells were allowed to shake for 1 hour, and then [$^{14}$C]AMG was quantitated on a TopCount scintillation counter. Controls were performed with and without NaCl. For determination of EC$_{50}$ values, 10 inhibitor concentrations were used over 2 log intervals in the appropriate response range, and triplicate plates were averaged across plates.

Ryan M J, Johnson G, Kirk J, Fuerstenberg S M, Zager R A and Torok-Storb B. 1994. HK-2: an immortalized proximal tubule epithelial cell line from normal adult human kidney. Kidney International 45: 48–57.

The following Working Examples represent preferred embodiments of the present invention. All temperatures are expressed in degrees Centigrade unless otherwise indicated.

EXAMPLE 1

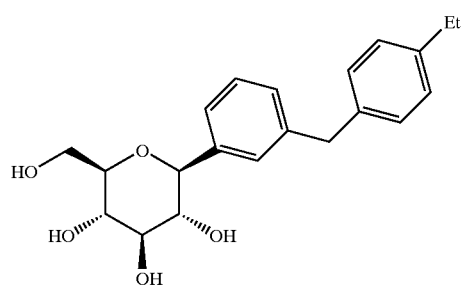

A. 3-Bromo-4'-ethylbenzylhydrol

Dry Mg turnings (4.4 g, 0.178 mol) under Ar were stirred overnight whereupon 100 mL of dry Et$_2$O was added followed by addition over 1 hr of p-bromoethylbenzene (22 g, 0.119 mol) in 20 mL of Et$_2$O. (In the event the reaction did not start, 0.5 ml of 1,2-dibromoethane was added). After stirring overnight, m-bromobenzaldehyde (11 g, 0.06 mol) in 20 mL of Et$_2$O was slowly added. The resulting light solution was monitored by HPLC over 4–6 hr to determine when complete. The reaction, after quenching with saturated aq. NH$_4$Cl, was extracted 3× with EtOAc. The combined organic layers were washed with brine, dried over Na$_2$SO$_4$ and concentrated using a rotary evaporator. The resulting yellow oil was chromatographed on silica gel using 5% EtOAc/hexane to elute nonpolar impurities and 7–9% EtOAc/hexane to elute 12.4 g (71%) of 3-bromo-4' (ethylbenzhydrol as a light yellow oil.

B. 3-Bromo-4'-ethyldiphenylmethane

To a stirred −30° solution of Part A 3-bromo-4'-ethylbenzhydrol (12.4 g, 0.0426 mol) in 120 mL of MeCN was added BF$_3$.Et$_2$O (6.04 g, 0.0426 mol) followed by Et$_3$SiH (9.9 g, 0.852 mol). The dark reaction after stirring 1 hr at −30° was warmed slowly to −5°. When complete by tlc, the reaction was quenched by addition of saturated aq. K$_2$CO$_3$. After addition of 100 mL of H$_2$O, the mixture was extracted 3× with Et$_2$O. The combined organic layers were washed with brine, dried over Na$_2$SO$_4$. After concentration using a rotary evaporator, 3-bromo-4'-ethyldiphenylmethane (11.17 g, 95%) was obtained as a light yellow oil that was used without further purification.

C.

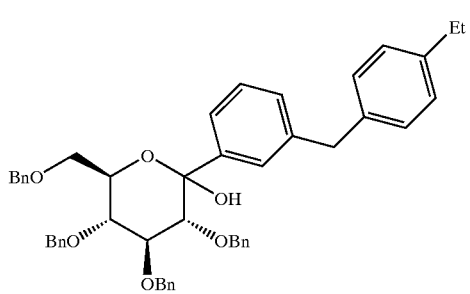

To a stirred −78° solution of Part B 3-bromo-4'-ethyldiphenylmethane (10.9 g, 0.04 mol) in 100 mL of dry THF under Ar was added 25.7 mL of 1.7 M t-BuLi in hexane over 20 min. After 1 hr 2,3,4,6-tetra-O-benzyl-β-D-glucolactone (23.5 g, 0.0437 mol) in 30 mL of THF was added over 15 min. The solution was stirred for 1 hr at −78° prior to quenching with saturated aq. $NH_4Cl$. After warming to 20°, the reaction was diluted 2 fold with EtOAc prior to washing with $H_2O$ followed by brine. After drying over $Na_2SO_4$ and concentration using a rotary evaporator, 29.2 g of the desired title lactol was obtained as a colorless syrup that was carried forward without further purification.

D.

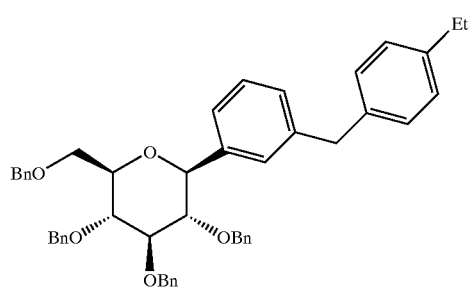

To a stirred −30° solution of Part C lactol (29.1 g, 0.04 mol) in 100 mL of MeCN was added $BF_3.Et_2O$ (5.62 g, 0.04 mol) followed by $Et_3SiH$ (9.21 g, 0.08 mol). After 2 hr, when tlc showed the reaction to be complete, saturated aq. $K_2CO_3$ was added and the suspension stirred 1 hr at 20° prior to diluting with $H_2O$ and $Et_2O$. The combined organic layers from 3 $Et_2O$ extractions were washed with brine, dried over $Na_2SO_4$, and concentrated using a rotary evaporator to yield 28.3 g of a light yellow syrup. Chromatography on silica gel with 5% EtOAc/hexane eluted nonpolar impurities followed slowly by the desired beta anomer and then the alpha anomer. Fractions enriched in the beta anomer could be further purified by either triterating with hexane or by recrystalization from EtOH to yield 6 g of the desired title beta tetra-O-benzyl C-glucoside. (Note when $Et_3SiH$ is the reducing agent, a 5:1 beta/alpha anomer mixture is obtained whereas when $iPr_3SiH$ is substituted a 30:1 mixture is obtained.)

E.

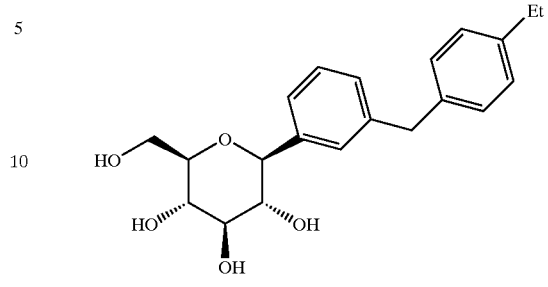

A solution of Part D tetra-O-benzyl C-glucoside (2.4 g, 3.35 mmol) in EtOAc (100 mL) containing 10% $Pd(OH)_2/C$ (0.35 g) was stirred overnight under 1 atmos. $H_2$. After HPLC showed the reaction to be complete, the catalyst was filtered and the solvent removed using a rotary evaporator to obtain 1.1 g of the desired beta C-glucoside (92%) as a white crystalline solid.

HPLC retention time: 7.04 min, 100% pure, YMC S5 C-18 4.6×50 mm column, 2.5 mL/min, detection at 220 nM; 8 min gradient 0–100% B hold 5 min at 100% B. Solvent A: 10% $MeOH/H_2O+0.2\%$ $H_3PO_4$. Solvent B: 90% MeOH/$H_2O+0.2\%$ $H_3PO_4$. $^1H$ NMR (500 MHz, $CD_3OD$) δ 7.27 (s, 1H), 7.23 (d, 2H, J=4.95 Hz), 7.1–7.0 (m, 5H), 4.08 (d, 1H, J=9.3 Hz), 3.91 (s, 2H), 3.9 (dd, 1H, J=2.2, 11 Hz), 3.68 (dd, 1H, J=5.5, 11.5 Hz), 3.5–3.35 (m, 4H), 2.57 (q, 2H, J=7.2 Hz), 1.18 (t, 3H, J=7.2 Hz) $^{13}C$ NMR (125 MHz, $CD_3OD$) δ 143, 142.8, 141, 140, 129.9, 129.6, 129.5, 129.1, 128.8, 126.7, 83.8, 82.3, 79.9, 76.4, 72.0, 63.2, 42.5, 29.4, 16.2. Anal. Calcd. for $C_{21}H_{26}O_5$ LC-MS [M+NH4] 376. found 376.

EXAMPLE 2

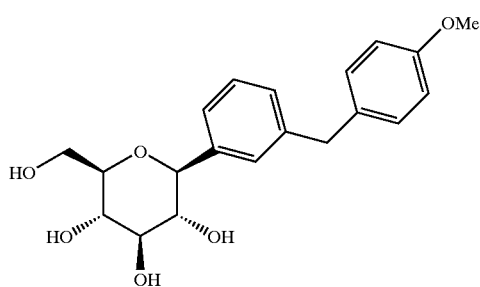

A. 3-Bromo-4'-methoxybenzhydrol

To a stirred −78° solution of m-dibromobenzene (70.9 g, 0.3 mol) in 200 mL of dry THF under Ar was added 117 mL of 2.56 M n-BuLi (0.3 mol) in hexane over 10 min. After 30 min, p-methoxybenzaldehyde (27.2 g, 0.02 mol) in 50 mL of THF was added over 20 min. The solution was stirred for 1 hr at −78° (complete by tlc) prior to quenching with saturated aq. $NH_4Cl$. After warming to 20°, the reaction was diluted 2 fold with EtOAc prior to washing with $H_2O$ followed by brine. After drying over $Na_2SO_4$ and concentration using a rotary evaporator, 103 g of 3-bromo-4'-methoxybenzhydrol was obtained as a yellow oil that was carried forward without further purification.

B. 3-Bromo-4'-methoxydiphenylmethane

To a stirred −40° solution of crude Part A 3-bromo-4'-methoxybenzhydrol (103 g, 0.2 mol) in 300 mL of MeCN was added Et$_3$SiH (64 mL, 0.4 mol) followed by BF$_3$·Et$_2$O (27.7 g, 0.2 mol). When complete by tlc, the reaction was quenched by addition of saturated aq. K$_2$CO$_3$ (25 mL). After addition of 100 mL of H$_2$O, the mixture was extracted 3× with EtOAc. The combined organic layers were washed with brine, dried over Na$_2$SO$_4$. After concentration using a rotary evaporator, the crude title 3-bromo-4'-methoxydiphenylmethane (92 g) was chromatographed on silica gel using 9% EtOAc/hexane to eluted 17 g of clean product followed by less pure fractions.

C.

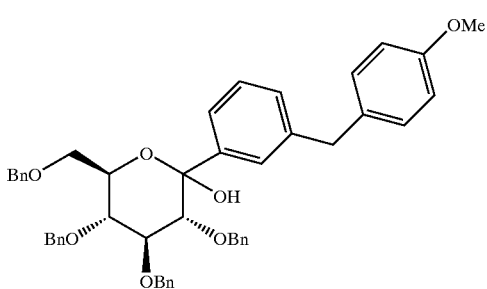

To a stirred −78° solution of Part B 3-bromo-4'-methoxydiphenylmethane (9.6 g, 0.035 mol) in 50 mL of dry THF under Ar was added 14 mL of 2.5 M n-BuLi in hexane over 5 min. After stirring 30 min, 2,3,4,6-tetra-O-benzyl-β-D-glucolactone (12.5 g, 0.023 mol) in 20 mL of THF was added over 10 min. The solution was stirred for 1 hr at −78° whereupon tlc analysis indicated the reaction was complete. After quenching with saturated aq. NH$_4$Cl (25 mL) and warming to 20°, the reaction was diluted with EtOAc (200 mL). The organic layer was washed with H$_2$O followed by brine. After drying over Na$_2$SO$_4$ and concentration using a rotary evaporator, the desired title lactol was chromatographed on silica gel using 12.5% EtOAC/hexane to elute 8.1 g of >90% lactol followed by 9.7 g of >80% purity.

D.

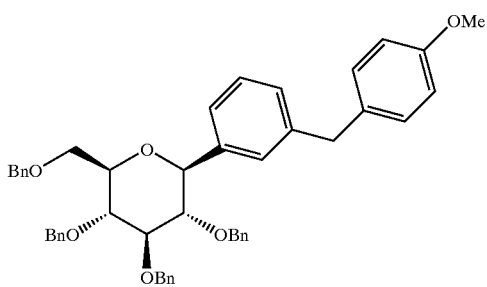

To a stirred −40° solution of Part C lactol (7.8 g, 0.019 mol) in 100 mL of MeCN was added Et$_3$SiH (3.42 mL, 0.04 mol) followed by BF$_3$·Et$_2$(1.37 mL, 0.02 mol). After 1 hr, when tlc showed the reaction to be complete, saturated aq. K$_2$CO$_3$ (10 mL) was added and the suspension stirred 1 hr at 20° prior to extracting 3× with EtOAc. The combined organic layers were washed with H$_2$O, brine, dried over Na$_2$SO$_4$, and concentrated using a rotary evaporator to yield 8 g of crude product. Chromatography on silica gel with 5% EtOAc/hexane eluted nonpolar impurities followed by 0.92 g of pure title β-tetra-O-benzyl C-glucoside followed by a 6.5 g containing both anomers.

E.

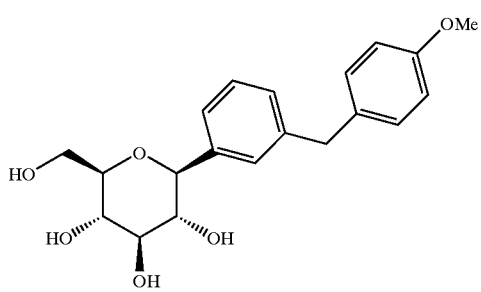

The above two fractions of Part D compound were hydrogenated separately over 10% Pd(OH)$_2$ (2% by weight) for overnight at 1 atomosphere H$_2$ in EtOAc (12.5 mL/g of Part D compound). After filtration and solvent removal, the hydrogenolysis product of the mixed fractions was purified by prep HPLC using a YMC S10 reverse phase column. The combined material yielded 1.85 g of pure β anomer as a white solid.

HPLC retention time: 6.04 min, Zorbax C-18 4.6×75 mm column, 2.5 mL/min, detection at 220 nM; 8 min gradient 0–100% B hold 3 min at 100% B. Solvent A: 10% MeOH/H$_2$O+0.2% H$_3$PO$_4$. Solvent B: 90% MeOH/H$_2$O+0.2% H$_3$PO$_4$. 1H NMR (400 MHz, CD$_3$OD) δ 7.28 (s, 1H), 7.24 (d, 2H, J=3 Hz), 7.09 (m, 3H), 6.79 (d, 2H, J=7 Hz), 4.08 (d, 1H, J=8.8 Hz), 3.88 (s, 2H), 3.75 (d, 1H, J=12 Hz), 3.73 (s, 3H), 3.65 (dd, 1H, J=12, 3 Hz), 3.4 (m, 4H). 13C NMR (100 MHz, CD$_3$OD) δ 158.6, 142.1, 140.2, 133.8, 130.0, 128.7, 128.6, 128.3, 125.8, 82.9, 81.3, 79.0, 75.5, 71.1, 62.5, 55.1, 41.1. Anal. Calcd. for C$_{20}$H$_{24}$O$_6$ LC-MS (M−H) 359. found 359.

EXAMPLE 3

A.

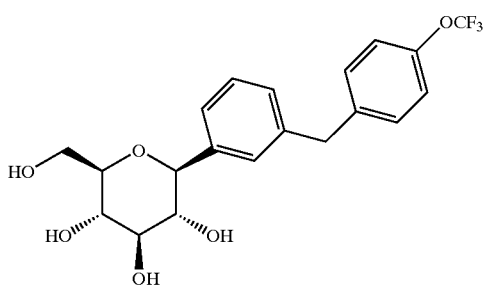

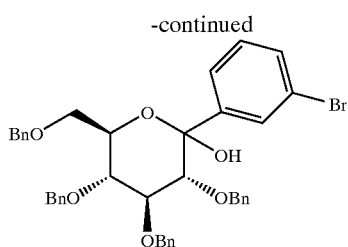

To a stirred −78° solution of m-dibromobenzene (12.6 g, 53 mmol) in 50 mL of dry THF under Ar was added 20 mL of 2.56 M n-BuLi (51 mmol) in hexane over 10 min. After 40 min, 2,3,4,6-tetra-O-benzyl-β-D-glucolactone (12 g, 22 mmol) in 30 mL of THF was added over 15 min. The solution was stirred for 1 hr at −78° (complete by tlc) prior to quenching with saturated aq. NH₄Cl (40 mL). After warming to 20°, the reaction was diluted 2 fold with EtOAc prior to washing with H₂O followed by brine. After drying over Na₂SO₄ and concentration using a rotary evaporator, 20 g of crude title lactol was obtained as an oil that was carried forward without further purification.

B.

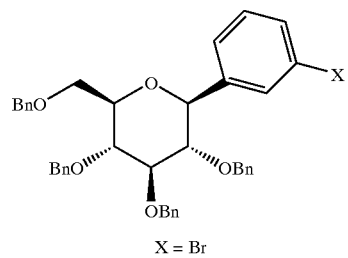

X = Br

To a stirred −45° solution of crude Part A lactol (20 g, 0.2 mol) in 60 mL of MeCN was added Et₃SiH (7.8 mL, 45 mmol) followed by slow addition over 20 min of BF₃·Et₂O (4.2 mL, 22 mmol). When complete by tlc after an hour, the reaction was quenched by addition of saturated aq. K₂CO₃ (25 mL) and the mixture was extracted 3× with EtOAc. The combined organic layers were washed with brine, dried over Na₂SO₄ and concentrated using a rotary evaporator. The resulting oil was triterated with 50 mL hexane whereupon solid precipitated after standing for 1 hr. This material was collected by filtration, washed with cold hexane twice and air dried to yield 8.9 g of the desired title β-m-bromophenyl-C-glucoside.

C.

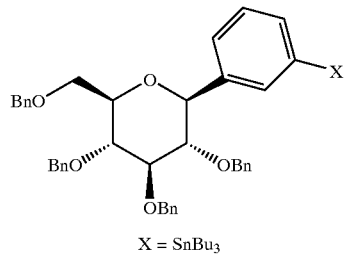

X = SnBu₃

A solution of Part B β-m-bromophenyl C-glucoside (1.36 g, 2 mmol), Pd(PPh₃)₄ (70 mg, 0.06 mmol), and hexabutyldistannane (2.724 g, 6 mmol) in dry toluene (10 mL) was heated with stirring under Ar at 80° for 15 hr. After removal of toluene using a rotary evaporator, the residue was chromatographed on silica gel using 12:1 EtOAc/hexane to elute the desired title aryl stannane (761 mg), plus mixed fractions, which after a second column yielded an additional 92 mg of clean title stannane for a total yield of 48%, followed by 230 mg of recovered starting Part B β-m-bromophenyl-C-glucoside.

D.

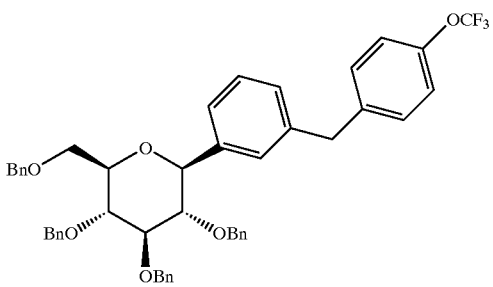

A mixture of Part E stannane (2.66 g, 3 mmol), p-trifluoromethoxybenzyl chloride (1.04 g, 6 mmol), and Pd(PPh₃)₄ (100 mg, 0.09 mmol) was refluxed under Ar in THF (1 ml) for 15 hr. After removal of THF with a rotary evaporator, the residue was chromatographed on silica gel using 10:1 hexane/EtOAc to elute 1.3 g of the desired title tetrabenzyl ether.

E

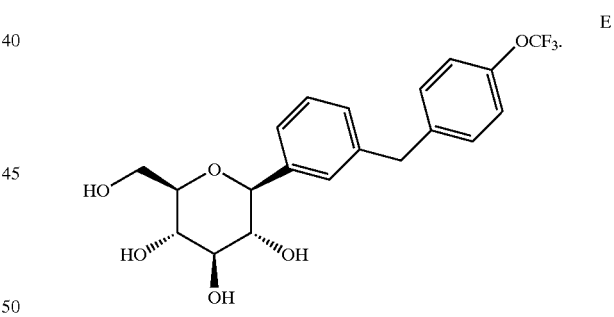

Conversion to the final free glucoside was achieved by stirring 295 mg of Part D tetrabenzyl ether with Pd(OH)₂ (15 mg) in EtOAc (3 mL) under 1 atmos of H₂ for 15 hr. The title product (104 mg) was isolated after filtration, Prep HPLC, and removal of solvent.

HPLC retention time: 7.21 min, Zorbax C-18 4.6×75 mm column, 2.5 mL/min, detection at 220 nM; 8 min gradient 0–100% B hold 3 min at 100% B. Solvent A: 10% MeOH/H2O+0.2% H₃PO₄. Solvent B: 90% MeOH/H₂O+0.2% H₃PO₄. 1H NMR (400 MHz, CD₃OD) δ 7.3 (m, 5H), 7.15 (m, 3H), 4.10 (d, 1H, J=8.8 Hz), 3.99 (s, 2H), 3.9 (d, 1H, J=12 Hz), 3.7 (dd, 1H, J=12, 3 Hz), 3.4 (m, 4H). Anal. Calcd. for C₂₀H₂₁F₃O₆ LC-MS (M−H) 413. found 413

EXAMPLE 4

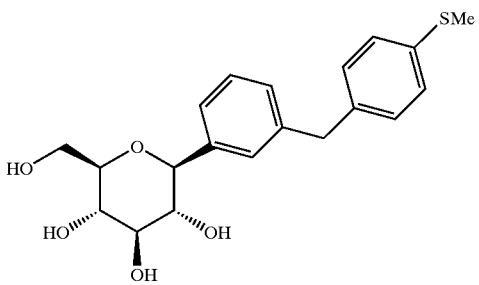

A.

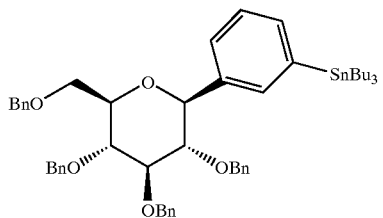

A mixture of Example 3 Part B β-m-bromophenyl-C-glucoside (3.0 g, 4.41 mmol) and Pd(PPh₃)₄ (153 mg, 0.13 mmol), and hexabutyldistannane (6.0 g, 13.2 mmol) in dry toluene (5 mL) was heated with stirring under Ar at 88° for 3 hr whereupon tlc analysis indicated the reaction was 90% complete. The reaction was terminated after a total of 5 hr. After removal of toluene using a rotary evaporator, the residue was chromatographed on silica gel using 1:8 EtOAc/hexane to elute the 2.95 g of desired aryl stannane.

B.

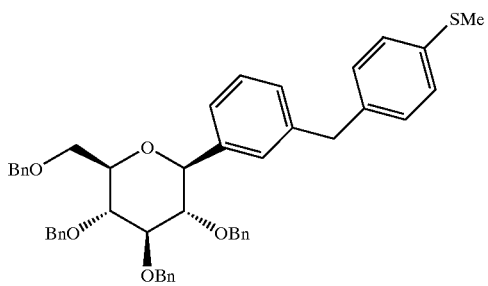

A mixture of Part A stannane (2.66 g, 3 mmol), p-methylthiobenzyl chloride (1.04 mg, 6.0 mmol), and tetrakis(triphenylphosphine)palladium (100 mg, 0.09 mmol) was refluxed under Ar in THF (5 mL) for 15 hr. After removal of THF with a rotary evaporator, the residue was chromatographed on silica gel using 6:1 hexane/EtOAc to elute 1.2 g of the desired title tetra-o-benzyl ether followed by 600 mg of title tetra-o-benzylether containing Ph₃P.

C.

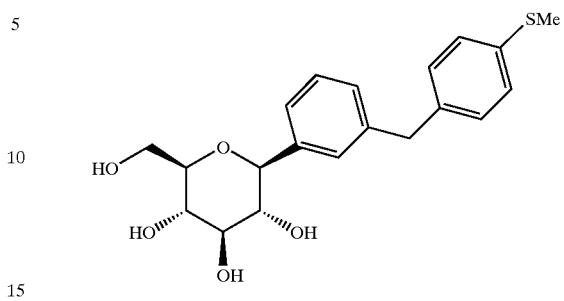

1 M BCl₃/CH₂Cl₂ (6 mL, 8 mmol) was added over 5 minutes to a stirred −78° solution of Part B tetrabenzyl ether (295 mg, 0.4 mmol) under Ar in CH₂Cl₂ (0.25 ml). After 30 min, when tlc analysis indicated the reaction was complete, 30 mL of 2:1 CH₂Cl₂/PhMe followed by 2 mL of MeOH were added. The volume was reduced by half using a rotary evaporator and 10 mL of MeOH added. After repeating this process 3x, all the volatiles were removed under vacuum. The residue was chromatographed on silica gel using 5% MeOH/CH₂Cl₂ to eluted 143 mg of the desired glucoside in 90% purity. This material was further purified by reverse phase preparative HPLC to yield 104 mg of the final desired glucoside.

HPLC retention time: 6.69 min, Zorbax C-18 4.6×75 mm column, 2.5 mL/min, detection at 220 nM; 8 min gradient 0–100% B hold 3 min at 100% B. Solvent A: 10% MeOH/H₂O+0.2% H₃PO₄. Solvent B: 90% MeOH/H₂O+0.2% H₃PO₄. 1H NMR (400 MHz, CD₃OD) δ 7.27 (s, 1H), 7.25 (d, 2H, J=2 Hz), 7.15 (m, 5H), 4.09 (d, 1H, J=8.8 Hz), 3.92 (s, 2H), 3.86 (d, 1H, J=12 Hz), 3.68 (dd, 1H, J=12, 3 Hz), 3.4 (m, 4H), 2.43 (s, 3H). Anal. Calcd. for $C_{20}H_{24}O_6S$ LC-MS (M−H) 375. found 375.

EXAMPLE 5

A.

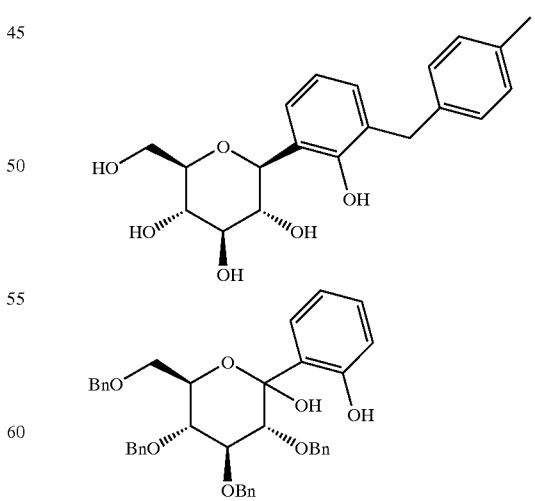

To a stirred suspension of 60% NaH (180 mg, 4.5 mmol) in THF (7 mL) under Ar was added 2-bromophenol (350 μL, 3 mmol). After stirring for 15 min, the reaction was cooled to −78° and 1.4 M t-BuLi/hexane (2.36 mL, 3.3 mmol) was added dropwise. After 10 min, the solution was transferred via cannula to a stirred −78° solution of 2,3,4,6-tetra-O-benzyl-β-D-glucolactone (1.62 g, 3.0 mmol) in THF (5 mL). The reaction was quenched after 15 min by slow addition of sat. NH$_4$Cl/H$_2$O and then allowed to warm to 20° whereupon 200 mL of EtOAc was added. The organic layer was washed successively with H$_2$O and brine, dried over MgSO$_4$, and concentrated. Chromatography on silica gel with 3:1 hexane/EtOAc yielded 390 mg of the desired title lactol.

B.

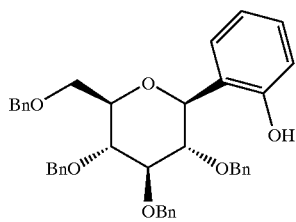

To a stirred 3:1 mixture of MeCN/CH$_2$Cl$_2$ (4 mL) containing Part A lactol (390 mg, 0.62 mmol) at −30° was added Et$_3$SiH (197 μL, 1.23 mmol) and BF$_3$·Et$_2$(78 μL, 0.62 mmol). After 1 hr the reaction was quenched by addition of 1 mL of sat. K$_2$CO$_3$, warmed to 20° and diluted with 100 mL EtOAc. The organic layer was washed successively with H$_2$O and brine, dried over MgSO4, and concentrated. Chromatography on silica gel with 3:1 hexane/EtOAc yielded 269 mg of desired title phenolic C-glucoside.

C.

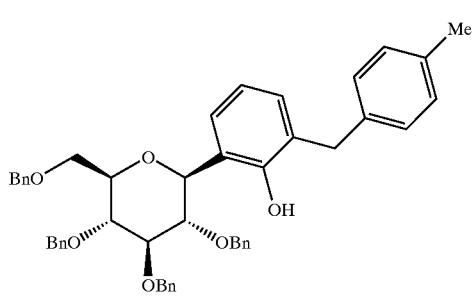

To a PhMe solution (1.1 mL) of Part B phenol (139 mg, 0.22 mmol) under Ar was added 60% NaH (11 mg, 0.27 mmol). After 10 min, 4-methylbenzyl bromide (46 mg, 0.25 mmol) was added as a solid to the blue solution which was then heated at 80° for 3.5 hr until complete by tlc analysis. After cooling followed by addition of aqueous NH$_4$Cl, the reaction was diluted with EtOAc. The organic layer was washed successively with H$_2$O and brine, dried over MgSO$_4$, and concentrated. Chromatography on silica gel with 5:1 hexane/EtOAc yielded 71 mg of the desired title tetra-O-benzylglucoside.

D.

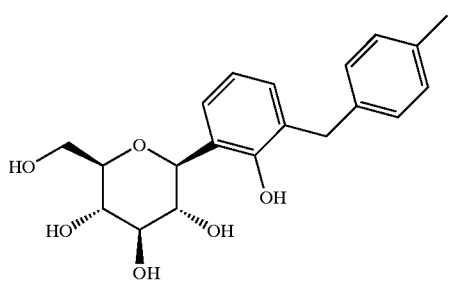

Subsequent hydrogenolysis of Part C tetra-O-benzyl glucoside over Pd/C in MeOH under 1 atmos H$_2$ yielded the final title product which was purified by preparative HPLC using a C18 reverse phase column a 45–90% MeOH/H$_2$O gradient over 10 min to elute the desired β-C-glucoside (2 mg).

HPLC retention time: 6.754 min, 100% pure, YMC S3 ODS 4.6×50 mm, 2.5 mL/min, detection at 220 nM; 8 min gradient 0–100% B hold 5 min at 100% B. Solvent A: 10% MeOH/H$_2$O+0.2% H$_3$PO$_4$. Solvent B: 90% MeOH/H$_2$O+ 0.2% H$_3$PO$_4$. $^1$H NMR (500 MHz, CD$_3$OD) δ 7.15 (dd, 1H, J=1.1, 7.7 Hz), 7.07 (d, 2H, J=8.3 Hz), 7.02 (d, 2H, J=8.3 Hz), 6.96 (dd, 1H, J=1.2, 7.7 Hz), 6.77 (t, 1H, J=7.7 Hz), 4.44 (d, 1H, J=8.8 Hz), 3.89 (s, 2H), 3.87 (d, 1H, J=2.2 Hz), 3.75 (dd, 1H, J=4.9, 12.1), 3.49–3.41 (m, 4H), 2.26 (s, 3H). Anal. Calcd. for C$_{20}$H$_{24}$O$_6$ LC-MS [M+H] 361. found 361.

EXAMPLE 6

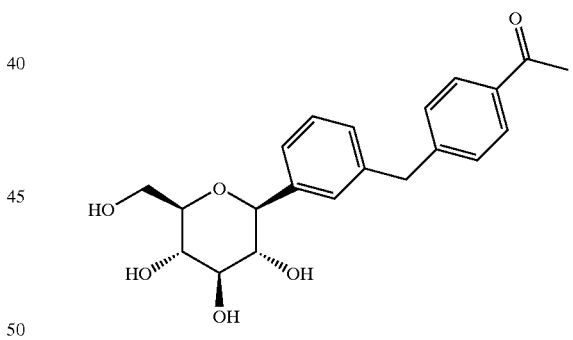

A. p-Chloromethylacetophenone

To a stirred solution of p-chloromethylbenzoyl chloride (390 mg, 2.06 mmol) in 8 mL THF at −20° under Ar was added tributylphosphine (406 mg, 2.29 mMol). After stirring the resulting yellow solution for 20 min at −20°–−15°, 0.7 mL of 3M methyl magnesium bromide in ether (2.1 mmol) was added in one portion to generate a red solution which subsequently became orange over a 10 min period. The reaction was quenched by addition of 1N aq. HCl. After dilution with H$_2$O, the mixture was extracted 3× with EtOAc, washed with H$_2$O prior to drying over Na$_2$SO$_4$. The residue obtained after removal of volatiles was chromatographed on silica gel using 5% EtOAc/hexane to elute 171 mg (50%) of p-chloromethylacetophenone.

B.

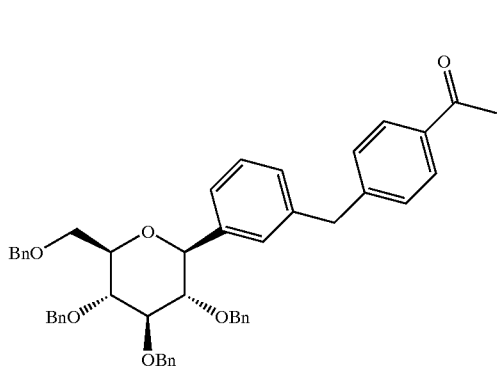

A mixture of the stannane described in Example 3 Part C (300 mg, 0.33 mmol), p-chloromethylacetophenone (114 mg, 0.66 mmol), and Pd(PPh$_3$)$_4$ (20 mg, 0.09 mmol), triphenylphosphine oxide (180 mg, 0.65 mmol), K$_2$CO$_3$ (75 mg, 0.55 mmol) was heated at 70° under Ar in THF (0.3 ml) for 16 hr. After removal of THF with a rotary evaporator, the residue was chromatographed on silica gel using 20:1 to 10:1 hexane/EtOAc to elute the desired tetrabenzyl ether (170 mg, 70%).

C.

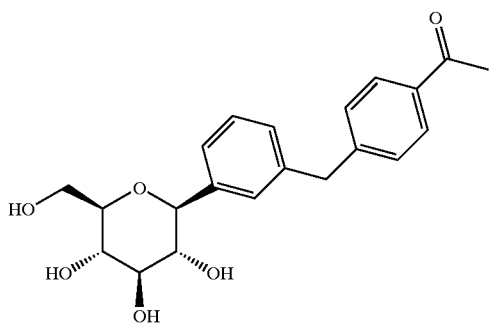

A solution of Part B tetrabenzyl ether (60 mg, 0.08 mmol) in CH$_2$Cl$_2$ (5 mL) under Ar was cooled to −78° prior to the addition of 0.8 mL of 1 M BCl$_3$ in CH$_2$Cl$_2$. After stirring for 1 hr at −78°, a second 0.8 mL portion of 1 M BCl$_3$ was added to the stirred reaction. After a second hour, 0.5 mL of PhMe was added followed by dropwise addition of 0.5 mL of MeOH. The volatiles were removed using a rotary evaporator; the process repeated after addition of 3 mL of a 2:1 mixture of CH$_2$Cl$_2$/MeOH. Chromatography of the resulting residue on silica gel eluting with 5% MeOH/EtOAc yielded 20 mg of tetraol final product in 67% yield.

HPLC retention time: 2.35 min, 100% pure, YMC S3 ODS 4.6×50 mm, 2.5 mL/min, detection at 220 nM; 4 min gradient 0–100% B hold 4 min at 100% B. Solvent A: 10% MeOH/H$_2$O+0.2% H$_3$PO$_4$. Solvent B: 90% MeOH/H$_2$O+ 0.2% H$_3$PO$_4$. $^1$H-NMR (500 MHz, CD$_3$OD): δ 7.88 (d, 2H), 7.27–7.34 (m, 5H), 7.13 (d, 1H), 4.09 (d, 1H), 4.03 (s, 2H), 3.85 (d, 1H), 3.68 (dd, 1H), 3.35–3.48 (m, 4H), 2.55 (s, 3H) $^{13}$C-NMR (500 MHz, CD$_3$OD): δ 200.3, 148.8, 141.4, 141.2, 136.3, 130.2, 129.7, 129.6, 129.3, 127.0, 83.6, 82.2, 79.8, 76.4, 71.9, 63.1, 42.7, 26.6 Anal. Calcd. for C$_{21}$H$_{24}$O$_6$ LC-MS (M+NH4+): 390.2. found 390.2.

EXAMPLE 7

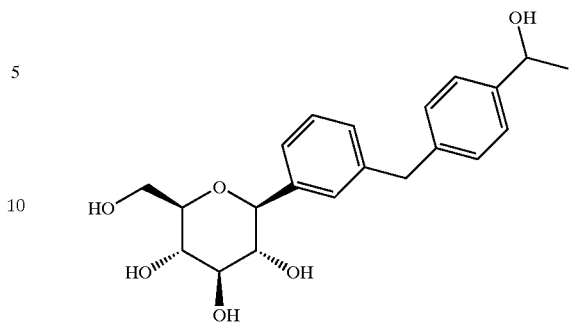

A stirred solution of the final product of Example 6 (15 mg, 0.04 mmol) in 5 mL of EtOH was cooled to −20° whereupon NaBH$_4$ (5 mg, 0.13 mmol) was added. After 20 min being complete by tlc analysis, the reaction was quenched with a few drops of saturated aq. NH$_4$Cl. After removal of the volatiles, the residue was chromatographed on silica gel. Elution with 5% MeOH/EtOAc yielded 10 mg (67%) of the desired product.

HPLC retention time: 5.2 min, 100% pure, YMC S3 ODS 4.6×50 mm, 2.5 mL/min, detection at 220 nM; 8 min gradient 0–100% B hold 5 min at 100% B. Solvent A: 10% MeOH/H$_2$O+0.2% H$_3$PO$_4$. Solvent B: 90% MeOH/H$_2$O+ 0.2% H$_3$PO$_4$. $^1$H-NMR (500 MHz, CD$_3$OD): δ 7.21–7.32 (m, 5H), 7.16 (d, 2H), 7.10–7.11 (m, 1H), 4.77 (q, 1H), 4.08 (d, 1H), 3.94 (s, 2H), 3.86 (dd, 1H), 3.68 (dd, 1H), 3.34–3.48 (m, 4H), 1.40 (d, 3H) $^{13}$C-NMR (500 MHz, CD$_3$OD) δ 145.2, 142.5, 141.5, 140.9, 129.8, 129.6, 129.5, 129.2, 126.7, 126.6, 83.7, 82.2, 79.8, 76.4, 72.0, 63.2, 42.5, 25.5 Anal. Calcd. for C$_{21}$H$_{26}$O$_6$ LC-MS (M+NH4+): 392.2. found 392.1.

EXAMPLE 8

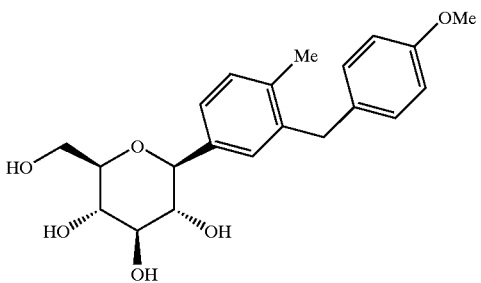

A. 5-Bromo-2-methylbenzoic Acid

A mixture of o-toluic acid (28 g, 206 mmol), iron powder (0.74 g, 13 mmol), and Br$_2$ (42 g, 260 mmol) were stirred at 0° for 2 hr. At this point the reaction, which had proceeded ~40%, was diluted with 25 mL of CH$_2$Cl$_2$ to facilitate stirring. The reaction was then heated at 45° for 16 hr to drive to completion. Upon cooling, the reaction was diluted with CH$_2$Cl$_2$, washed 2× with 10% NaHSO$_3$, 1× with brine prior to drying over Na$_2$SO$_4$. After removal of the volatiles, the residue comprising a 2:1 mixture of 5-bromo to 3-bromotoluic acid was recrystallized from 95% EtOH to yield 14.4 g of 5-bromo-2-methylbenzoic acid.

B. 5-Bromo-2-methyl-4′methoxybenzophenone

To a stirred suspension of 5-bromo-2-methylbenzoic acid (1.29 g, 6 mmol) in 12 mL of CH$_2$Cl$_2$ containing oxalyl chloride (8 mmol) was added 2 drops of DMF. Once the vigorous evolution of gas ceased, the reaction was stirred 6 hr prior to removal of the volatiles using a rotary evaporator. After dissolving the crude 5-bromo-2-methylbenzoyl chloride in 15 ml of CS2, the stirred mixture was cooled to 4° prior to adding anisole (0.7 g, 6.6 mmol) followed by $AlCl_3$ (1.7 g, 12 mmol). The reaction, after warming to 20° over 1 hr, was stirred for 15 hr prior to quenching with 1N HCl. Subsequently, the suspension was diluted with 50 ml $H_2O$ and stirred until all solids were in solution. The mixture was extracted 3× with EtOAc. The combined organic extracts were washed 1× with 1N HCl, $H_2O$, aq $NaHCO_3$, and brine prior to drying over $Na_2SO_4$. After removal of the volatiles, the resulting tan solid was recrystallized from 95% EtOH to yield 1.6 g of 5-bromo-2-methyl-4'-methoxybenzophenone.

C. 5-Bromo-2-methyl-4'-methoxydiphenylmethane

A solution of $Et_3SiH$ (2.5 mL, 15.5 mmol), $BF_3 \cdot Et_2O$ (1.3 mL, 10 mmol), and 5-bromo-2-methyl-4'-methoxybenzophenone (1.6 g, 5.25 mmol) in 11 mL of a 1:4 mixture $CH_2Cl_2$/MeCN was stirred overnight at 20°. Since by HPLC 5% of starting ketone remained, the solution was heated to 40° for 1 hr prior to quenching with 10% NaOH. After dilution with $H_2O$, the reaction was extracted 3× with EtOAc. The combined organic layers were washed 2× with $H_2O$ and once with brine before drying over $Na_2SO_4$. After removal of the volatiles, the residue was chromatographed on silica gel using hexane to elute 5-bromo-2-methyl-4'-methoxydiphenylmethane as a colorless oil (1.4 g, 95%)

D.

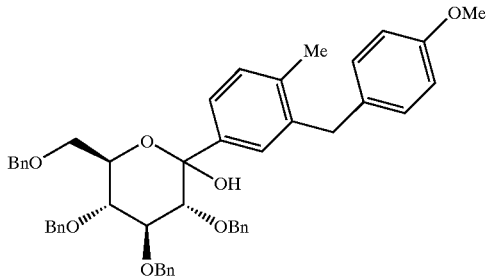

To a stirred −78° solution of Part C 5-bromo-2-methyl-4'-methoxydiphenylmethane (0.43 g, 1.5 mmol) in 7 mL of dry THF under Ar was added dropwise 0.9 mL of 1.8 M n-BuLi in hexane. After 2 hr, 2,3,4,6-tetra-O-benzyl-β-D-glucolactone (0.88 g, 1.6 mmol) in 3 mL of THF was added over 1 min. The solution was stirred for 2 hr at −78° prior to quenching with saturated aq. $NH_4Cl$. After warming to 20°, the reaction was diluted 2 fold with $H_2O$ prior to 3 extractions with EtOAc. The combined EtOAc fractions were washed with brine and dried over $Na_2SO_4$. After concentration using a rotary evaporator, 1.1 g of the desired title lactol was obtained as a colorless syrup that was carried forward without further purification.

E.

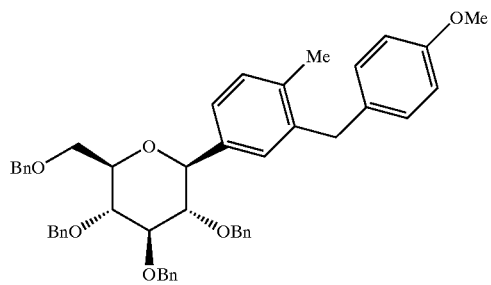

To a stirred −30° solution of Part D lactol (1.1 g, 1.47 mmol) in 10 mL of MeCN was added $iPr_3SiH$ (0.7 g, 4.5 mmol) followed by $BF_3 \cdot Et_2O$ (0.38 g, 2.6 mmol). After 3 hr at −40°–−30°, the reaction was complete by tlc showed. Saturated aq. $K_2CO_3$ was added and the suspension stirred 1 hr at 20° prior to diluting with $H_2O$ and EtOAc. The combined organic layers from 3 EtOAc extractions were washed with brine, dried over $Na_2SO_4$, and concentrated using a rotary evaporator to yield 1.2 g of a light yellow syrup. Chromatography on silica gel with 10% EtOAc/hexane eluted nonpolar impurities followed by the desired beta C-arylglucoside (0.54 g).

F.

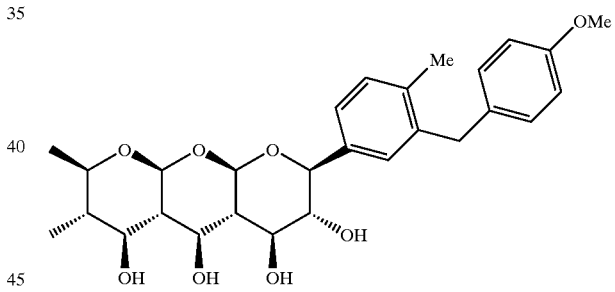

A solution of Part E tetra-O-benzyl C-glucoside (515 mg, 0.7 mmol) in EtoAc (10 mL) containing 10% $Pd(OH)_2$/C (80 mg) was stirred overnight under 1 atmos. $H_2$. After HPLC showed the reaction to be complete, the catalyst was filtered and the solvent removed using a rotary evaporator to obtain a white glassy solid that was further purified by preparative HPLC using a $C_{18}$ reverse phase column to obtain 220 mg of the desired beta C-glucoside as a colorless syrup.

HPLC retention time: 6.43 min, 100% pure, YMC S5 C-18 4.6×50 mm column, 2.5 mL/min, detection at 220 nM; 8 min gradient 0–100% B hold 5 min at 100% B. Solvent A: 10% MeOH/$H_2O$+0.2% $H_3PO_4$. Solvent B: 90% MeOH/$H_2O$+0.2% $H_3PO_4$. $^1$H NMR (500 MHz, $CD_3OD$) δ 7.20 (s, 1H), 7.18 (d, 1H, J=7 Hz), 7.11 (d, 1H, J=7Hz), 6.89 (ABq, 4H), 4.07 (d, 1H, J=9 Hz), 3.90 (s, 2H), 3.87 (m, 1H), 3.70 (s, 3H), 3.68 (dd, 1H), 3.48–3.30 (m, 4H), 2.16 (s, 3H). $^{13}$C NMR (125 MHz, $CD_3OD$) δ 159.3, 140.3, 138.3, 137.4, 133.7, 131.0, 130.8, 130.6, 126.9, 114.7, 83.5, 82.1, 79.8, 76.3, 71.9, 63.1, 55.6, 59.6, 19.5. Anal. Calcd. for $C_{21}H_{26}O_6$ LC-MS [M−H] 373. found 373.

EXAMPLE 9

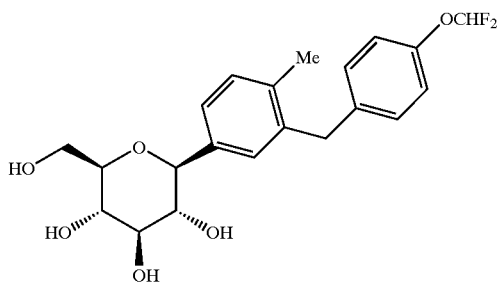

A. 5-Bromo-2-methyl-4'-hydroxydiphenylmethane

To a stirred −78° 10 mL $CH_2Cl_2$ solution of 5-bromo-2-methyl-4'-methoxydiphenylmethane (1.0 g, 3.4 mmol)(See Example 8, Part C for preparation) was added 4.12 mL of a 1M $BBr_3/CH_2Cl_2$. After 2 hr, the reaction was maintained at −40° for 20 hr whereupon HPLC indicated no starting ether remained. The reaction was quenched with aq. NaOH, extracted 3× with $CH_2Cl_2$, washed with brine prior to drying over $Na_2SO_4$. After removal of the volatiles, 0.84 g of 5-bromo-2-methyl-4'-hydroxydiphenylmethane was obtained as a syrup which was used without further purification.

B. 5-Bromo-2-methyl-4'benzyloxydiphenylmethane

A 10 mL DMF solution containing Part A 5-bromo-2-methyl-4'-hydroxydiphenylmethane (735 mg, 2.65 mmol), benzyl bromide (548 mg, 3.2 mmol), and $K_2CO_3$ (732 mg, 5.3 mmol) was stirred overnight. The reaction was then heated at 60° for 6 hr to drive the conversion from 80% to 100%. After dilution with $H_2O$, the reaction was extracted 3× with EtOAc. The combined EtOAc layers were washed with $H_2O$ and brine prior to drying over $Na_2SO_4$. The residue, after solvent removal under vacuum was chromatographed on silica gel using 3% EtOAc/hexane to elute 785 mg of 5-bromo-2-methyl-4'-benzyloxydiphenylmethane as a colorless syrup.

C.

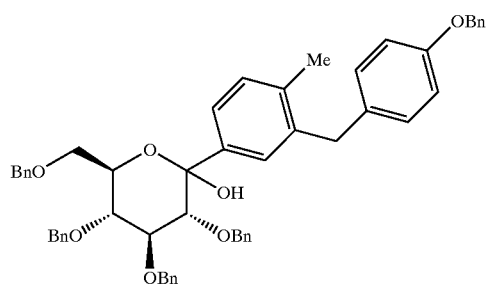

To a stirred −78° solution of Part B 5-bromo-2-methyl-4'-benzyloxydiphenylmethane (0.43 g, 1.2 mmol) in 7 mL of dry THF under Ar was added 0.68 mL of 1.9 M n-BuLi in hexane dropwise. After 30 min, 2,3,4,6-tetra-O-benzyl-β-D-glucolactone (0.7 g, 1.3 mmol) in 3 mL of THF was added over 1 min. The solution was stirred for 0.75 hr at −78° prior to quenching with saturated aq. $NH_4Cl$. After warming to 20°, the reaction was diluted 2 fold with $H_2O$ prior to 3 extractions with EtOAc. The combined EtOAc fractions were washed with brine and dried over $Na_2SO_4$. After concentration using a rotary evaporator, 0.96 g of the desired title lactol was obtained as a colorless syrup that was carried forward without further purification.

D.

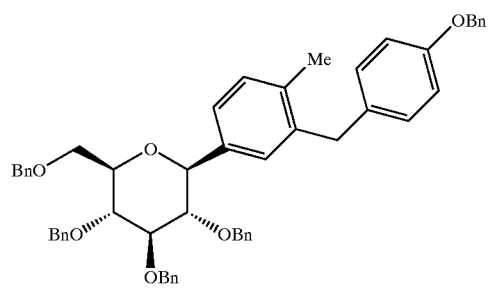

To a stirred −30° solution of Part C lactol (0.96 g, 1.16 mmol) in 10 mL of MeCN was added $iPr_3SiH$ (0.37 g, 2.3 mmol) followed by $BF_3·Et_2O$ (0.2 g, 1.4 mmol). After 3 hr at −40°−−30°, saturated aq. $K_2CO_3$ was added and the suspension stirred 1 hr at 20° prior to diluting with $H_2O$ and EtOAc. The combined organic layers from 3 EtOAc extractions were washed with brine, dried over $Na_2SO_4$, and concentrated using a rotary evaporator to yield 1.2 g of a light yellow syrup. Chromatography on silica gel with 9% EtOAc/hexane eluted nonpolar impurities; 10% EtOAc/hexane eluted the desired beta C-arylglucoside (0.26 g).

E.

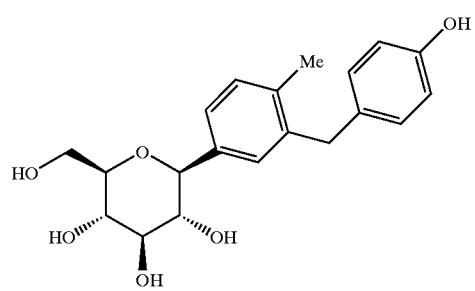

A solution of Part D penta-O-benzyl C-glucoside (255 mg, 0.31 mmol) in EtOAc (10 mL) containing 10% $Pd(OH)_2/C$ (65 mg) was stirred 24 hr under 1 atmos. $H_2$. After HPLC showed the reaction to be complete, the catalyst was filtered and the solvent removed using a rotary evaporator to obtain 115 mg of a white glassy solid that was used without further purification.

F.

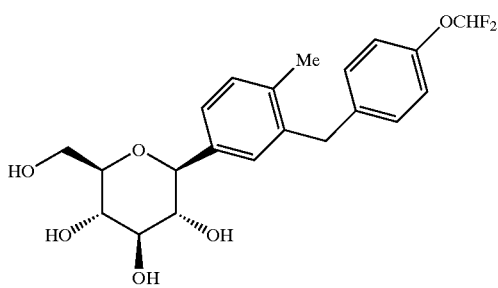

A threaded tube containing a magnetic stirrer, 4 mL of iPrOH and Part E phenolic C-glucoside (80 mg, 0.16 mmol) was cooled to −78° whereupon 1.5 g of CHClF₂ was added by condensing the gas. After adding 3 mL of 25% aq. NaOH, the tube was sealed with a Teflon stopper and heated to 70° for 2 hr. By HPLC reaction contained a 2:3 mixture of starting phenol to desired ether. (Efforts to drive the conversion by prolonged reaction times were not successful.) After cooling, sufficient 1N HCl was added to bring the pH to 2 whereupon most volatiles were removed using a rotary evaporator, The residue, after dissolution in 2:1 MeOH/H₂O was purified by preparative HPLC equipped with a YMC S5 C₁₈ reverse phase column (20×100 mm) employing a 10 min linear gradient with 45%–90% aq MeOH at 20 mL/min to yield 40 mg of the desired phenolic ether.

HPLC retention time: 6.6 min, 95% pure, YMC S5 C-18 4.6×50 mm column, 2.5 mL/min, detection at 220 nM; 8 min gradient 0–100% B hold 5 min at 100% B. Solvent A: 10% MeOH/H₂O+0.2% H₃PO₄. Solvent B: 90% MeOH/H₂O+0.2% H₃PO₄. $^1$H NMR (400 MHz, CD₃OD) δ 7.22 (s, 1H), 7.20 (m, 1H), 7.12 (m, 1H), 7.06 (ABq, 4H), 6.73 (t, 1H, J=27 Hz), 4.09 (d, 1H, J=9 Hz), 3.98 (s, 2H), 3.89 (d, 1H), 3.68 (dd, 1H), 3.47–3.30 (m, 4H), 2.17 (s, 3H). $^{13}$C NMR (100 MHz, CD₃OD) δ 138.7, 138.2, 137.7, 136.6, 130.3, 130.2, 130.1, 126.4, 119.3, 117.0, 82.7, 81.4, 79.0, 75.6, 71.1, 62.3, 49.0, 38.8, 18.6. Anal. Calcd. for $C_{21}H_{24}F_2O_6$ LC-MS [M+NH4] 428. found 428.

EXAMPLE 10

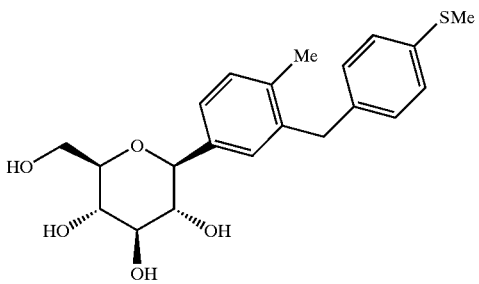

A. 5-Bromo-2-methyl-4'-thiomethylbenzophenone

AlCl₃ (535 mg, 4 mmol) was added to a 4° stirred 5 mL CS₂ solution of crude 5-bromo-2-methylbenzoyl chloride (466 mg, 2 mmol) (for preparation see Example 8, part B) and thioanisole (270 mg, 2.3 mmol). The reaction, after warming to 20° over 1 hr, was stirred for 2 hr prior to quenching with 1N HCl. Subsequently, the suspension was diluted with 50 ml H₂O and stirred until all solids were in solution. The mixture was extracted 3x with EtOAc. The combined organic extracts were washed 1× with 1N HCl, H₂O, aq NaHCO₃, and brine prior to drying over Na₂SO₄. After removal of the volatiles, the residue was chromatographed on silica gel using 15% EtOAc/hexane to elute 450 mg of 5-bromo-2-methyl-4'-thiomethylbenzophenone as a white solid.

B. 5-Bromo-2-methyl-4'-thiomethyldiphenylmethane

A solution of Et₃SiH (0.45 mL, 2.85 mmol), BF₃·Et₂O (0.3 mL, 2.4 mmol), and Part A 5-bromo-2-methyl-4'-thiomethylbenzophenone (450 mg, 1.4 mmol) in 3 mL of a 1:9 mixture CH₂Cl₂/MeCN was stirred overnight at 20°. After quenching with 10% NaOH and dilution with H₂O, the reaction was extracted 3× with EtOAc. The combined organic layers were washed 2× with H₂O and once with brine before drying over Na₂SO₄. After removal of the volatiles, the residue was chromatographed on silica gel using 5% EtOAc/hexane to elute 416 mg of 5-bromo-2-methyl-4'-thiomethyldiphenylmethane as a colorless oil.

C.

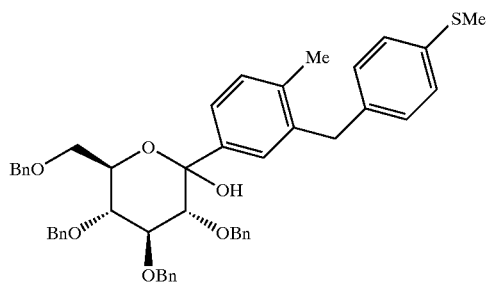

To a stirred −78° solution of Part B 5-bromo-2-methyl-4'-thiomethyldiphenylmethane (200 mg, 0.65 mmol) in 10 mL of dry THF under Ar was added dropwise 0.42 mL of 1.8 M n-BuLi in hexane. After 2 hr, this solution was transferred by cannula to a stirred −78° solution of 2,3,4,6-tetra-O-benzyl-β-D-glucolactone (0.88 g, 1.6 mmol) in 5 mL of THF. The solution was stirred for 2 hr at −78° before quenching with saturated aq. NH₄Cl. After warming to 20°, the reaction was diluted 2 fold with H₂O prior to 3 extractions with EtOAc. The combined EtOAc fractions were washed with brine and dried over Na₂SO₄. After concentration using a rotary evaporator, 550 mg of the desired title lactol was obtained as a colorless syrup that was carried forward without further purification.

D.

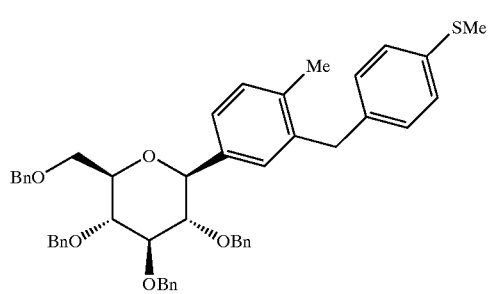

To a stirred −40° solution of Part C lactol (550 mg, 0.72 mmol) in 6 mL of MeCN was added iPr₃SiH (0.22 mL, 1.0 mmol) followed by BF₃·Et₂O (0.11 mL, 0.8 mmol). After 1.5 hr at −40°—−30°, when tlc showed the reaction to be complete, saturated aq. $K_2CO_3$ was added and the suspension stirred 1 hr at 20° prior to diluting with $H_2O$ and EtOAc. The combined organic layers from 3 EtOAc extractions were washed with brine, dried over $Na_2SO_4$, and concentrated using a rotary evaporator. Chromatography of the residue on silica gel using 9% EtOAc/hexane as eluant eluted 240 mg of the desired beta C-arylglucoside.

E.

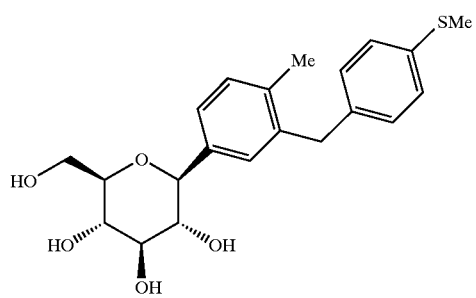

A solution of Part D tetra-O-benzyl C-glucoside (70 mg, 0.1 mmol) in EtSH (1.5 mL) containing $BF_3 \cdot Et_2O$ (0.24 mL, 2 mmol) was stirred at 200 for 2 hr. After 1 more hr following addition of an additional 0.12 mL of $BF_3 \cdot Et_2O$, the reaction was complete. The reaction was quenched by slow addition of 0.4 mL of pyridine prior to dilution with aq. $NH_4Cl$. The combined organic layers from 3 EtOAc extractions were washed with brine, dried over $Na_2SO_4$, and concentrated using a rotary evaporator. The residue was purified by preparative HPLC using a $C_{18}$ reverse phase column to obtain 20 mg of the desired beta C-glucoside as a white lyophilate after lyophilization.

HPLC retention time: 3.8 min, 95% pure, YMC S5 C-18 4.6×50 mm column, 2.5 mL/min, detection at 220 nM; 4 min gradient 0–100% B hold 4 min at 100% B. Solvent A: 10% $MeOH/H_2O+0.2\%$ $H_3PO_4$. Solvent B: 90% $MeOH/H_2O+ 0.2\%$ $H_3PO_4$. $^1H$ NMR (500 MHz, $CD_3OD$) δ 7.21–7.11 (m, 5H), 7.05 (d, 2H, J=8.0 Hz), 4.08 (d, 1H, J=9.1 Hz), 3.98 (s, 2H), 3.87 (d, 1H, J=12.6 Hz), 3.68 (dd, 1H, J=5.2, 12.1 Hz), 3.49–3.30 (m, 4H), 2.41 (s, 3H). $^{13}C$ NMR (125 MHz, $CD_3OD$) δ 139.8, 138.9, 138.4, 137.5, 137.1, 131.1, 130.9, 129.1, 130.3, 127.8, 127.1, 83.6, 82.2, 79.8, 76.4, 72.0, 63.2, 39.9, 19.5, 16.1. Anal. Calcd. for $C_{21}H_{26}O_5S$ LC-MS $[M+NH_4]$ 408. found 408.

EXAMPLE 11

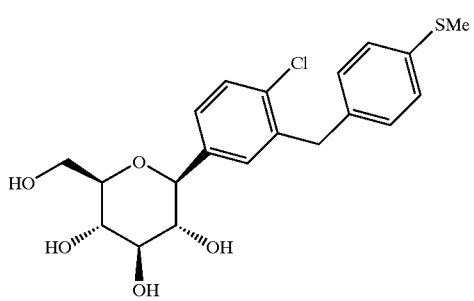

A. 5-Bromo-2-chloro-4'-thiomethylbenzophenone

To a stirred suspension of commercial 5-bromo-2-chlorobenzoic acid (506 mg, 2.12 mmol) in 10 mL of $CH_2Cl_2$ containing oxalyl chloride (2.4 mmol) was added 2 drops of DMF. Once the vigorous evolution of gas ceased, the reaction was stirred 1.5 hr before removal of the volatiles using a rotary evaporator. After dissolving the crude 5-bromo-2-chlorobenzoyl chloride in 8 ml of $CS_2$, the stirred mixture was cooled to 4° prior to adding thioanisole (260 mg, 2.12 mmol) followed by $AlCl_3$ (566 mg, 4.25 mmol). The reaction, after warming to 20° over 1 hr, was stirred for 20 hr prior to quenching with 1N HCl. Subsequently, the suspension was diluted with 50 ml $H_2O$ and stirred until all solids were in solution. The mixture was extracted 3× with EtOAc. The combined organic extracts were washed 1× with 1N HCl, $H_2O$, aq $NaHCO_3$, and brine prior to drying over $Na_2SO_4$. After removal of the volatiles, the 710 mg of crude of 5-bromo-2-chloro-4'-thiomethylbenzophenone was not further purified.

B. 5-Bromo-2-chloro-4' thiomethyldiphenylmethane

A solution of $Et_3SiH$ (1.4 mL, 8.8 mmol), $BF_3 \cdot Et_2O$ (0.83 mL, 6.6 mmol), and Part A 5-bromo-2-chloro-4'-thiomethylbenzophenone (710 mg, 2.1 mmol) in 10 mL of a 1:4 mixture $CH_2Cl_2/MeCN$ was stirred 2 hr at 20°. After quenching with 10% $NaHCO_3$ and dilution with $H_2O$, the reaction was extracted 3× with EtOAc. The combined organic layers were washed 2× with $H_2O$ and once with brine before drying over $Na_2SO_4$. After removal of the volatiles, the residue was chromatographed on silica gel using 5% EtOAc/hexane to elute 630 mg of 5-bromo-2-chloro-4'-thiomethyldiphenylmethane as a colorless oil.

C.

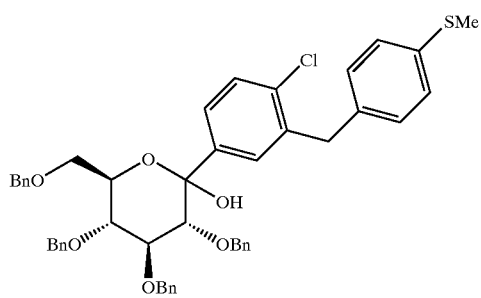

To a stirred −78° solution of Part B 5-bromo-2-chloro-4'-thiomethyldiphenylmethane (200 mg, 0.61 mmol) in 6 mL of dry THF under Ar was added 0.48 mL of 1.5 M n-BuLi in hexane dropwise. After 35 minutes, this solution was transferred by cannula to a stirred −78° solution of 2,3,4,6-tetra-O-benzyl-β-D-glucolactone (361 mg, 0.67 mmol) in 5 mL of THF. The solution was stirred for 1.5 hr at −78° prior to quenching with saturated aq. $NH_4Cl$. After warming to 20°, the reaction was diluted 2 fold with $H_2O$ prior to 3 extractions with EtOAc. The combined EtOAc fractions were washed with brine and dried over $Na_2SO_4$. After concentration using a rotary evaporator, the residue was chromatographed on silica gel using 20% EtOAc/hexane to elute 250 mg of the desired title lactol.

D.

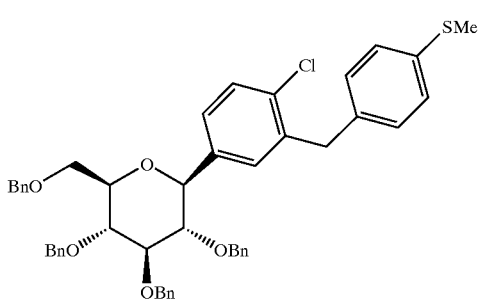

To a stirred −30° solution of Part C lactol (250 mg, 0.32 mmol) in 5 mL of MeCN was added iPr$_3$SiH (0.10 mL, 0.56 mmol) followed by BF$_3$·Et$_2$O (0.048 mL, 0.38 mmol). After 0.5 hr at −30°, when tlc showed the reaction to be complete, saturated aq. NaHCO$_3$ was added and the suspension stirred 1 hr at 20° prior to diluting with H$_2$O and EtOAc. The combined organic layers from 3 EtOAc extractions were washed with brine, dried over Na$_2$SO$_4$, and concentrated using a rotary evaporator. Chromatography of the residue on silica gel using 9% EtOAc/hexane as eluant eluted 200 mg of the desired beta C-arylglucoside.

E.

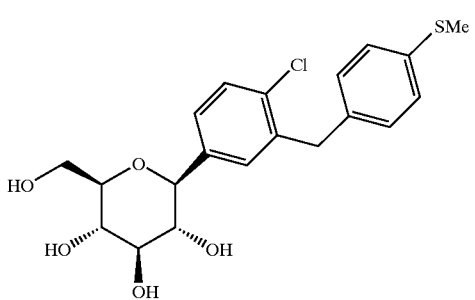

A solution of Part D tetra-O-benzyl C-glucoside (60 mg, 0.1 mmol) in EtSH (2 mL) containing BF$_3$·Et$_2$O (0.24 mL, 2 mmol) was stirred at 20° for 3 hr. The reaction was quenched by slow addition of 0.4 mL of pyridine prior to dilution with aq. NH$_4$Cl. The combined organic layers from 3 EtOAc extractions were washed with brine, dried over Na$_2$SO$_4$, and concentrated using a rotary evaporator. The residue was purified by preparative HPLC using a C$_{18}$ reverse phase column to obtain 21.5 mg of the desired beta C-glucoside as a white lyophilate after lyophilization.

HPLC retention time: 3.96 min, 95% pure, YMC S5 C-18 4.6×50 mm column, 2.5 mL/min, detection at 220 nM; 4 min gradient 0–100% B hold 4 min at 100% B. Solvent A: 10% MeOH/H$_2$O+0.2% H$_3$PO$_4$. Solvent B: 90% MeOH/H$_2$O+0.2% H$_3$PO$_4$. $^1$H NMR (400 MHz, CD$_3$OD) δ 7.36–7.27 (m, 3H), 7.15 (d, 2H, J=8.3 Hz), 7.11 (d, 2H, J=8.3 Hz), 4.10–4.04 (m, 3H), 3.87 (d, 1H, J=12 Hz), 3.70 (dd, 1H, J=7.1, 11.8 Hz), 3.47–3.26 (m, 4H), 2.42 (s, 3H). $^{13}$C NMR (100 MHz, CD$_3$OD) δ 140.1, 139.3, 138.0, 137.5, 134.5, 132.0, 130.4, 130.2, 128.4, 128.0, 82.9, 82.8, 82.2, 79.7, 76.5, 71.8, 63.1, 39.5, 16.1. Anal. Calcd. for C$_{20}$H$_{23}$ClO$_5$S LC-MS [M−H] 409. found 409.

EXAMPLE 12

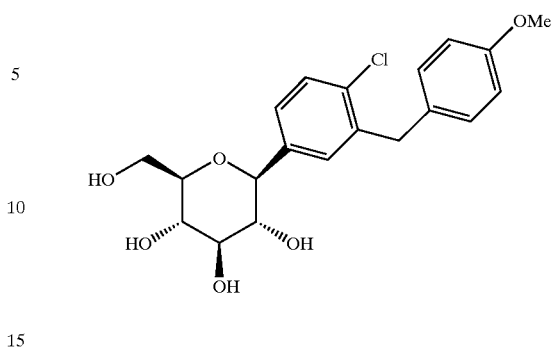

A. 5-Bromo-2-chloro-4'-methoxybenzophenone

To a stirred suspension of commercial 5-bromo-2-chlorobenzoic acid (506 mg, 2.12 mmol) in 10 mL of CH$_2$Cl$_2$ containing oxalyl chloride (2.4 mmol) was added 2 drops of DMF. Once the vigorous evolution of gas ceased, the reaction was stirred 1.5 hr prior to removal of the volatiles using a rotary evaporator. After dissolving the crude 5-bromo-2-chlorobenzoyl chloride in 8 ml of CS$_2$, the stirred mixture was cooled to 4° prior to adding anisole (240 mg, 2.12 mmol) followed by AlCl$_3$ (566 mg, 4.25 mmol). The reaction, after warming to 20° over 1 hr, was stirred for 20 hr prior to quenching with 1N HCl. Subsequently, the suspension was diluted with 50 ml H$_2$O and stirred until all solids were in solution. The mixture was extracted 3× with EtOAc. The combined organic extracts were washed 1× with 1N HCl, H$_2$O, aq NaHCO$_3$, and brine prior to drying over Na$_2$SO$_4$. After removal of the volatiles, the residue was chromatographed on silica gel using 15% EtOAc/hexane to elute 450 mg of 5-bromo-2-chloro-4'-methoxybenzophenone.

B. 5-Bromo-2-chloro-4'-methoxydiphenylmethane

A solution of Et$_3$SiH (0.45 mL, 2.85 mmol), BF$_3$·Et$_2$O (0.3 mL, 2.4 mmol), and 5-bromo-2-chloro-4'-methoxybenzophenone (450 mg, 1.4 mmol) in 3 mL of a 1:9 mixture CH$_2$Cl$_2$/MeCN was stirred overnight at 20°. After quenching with 10% NaOH and dilution with H$_2$O, the reaction was extracted 3× with EtOAc. The combined organic layers were washed 2× with H$_2$O and once with brine before drying over Na$_2$SO$_4$. After removal of the volatiles, the residue was chromatographed on silica gel using 2% EtOAc/hexane to elute 416 mg of 5-bromo-2-chloro-4'-methoxydiphenylmethane as a colorless oil.

C.

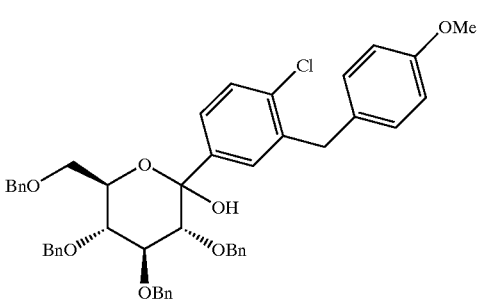

To a stirred −78° solution of Part B 5-bromo-2-chloro-4'-methoxydiphenylmethane (212 mg, 0.68 mmol) in 8 mL of dry THF under Ar was added 0.36 mL of 1.9 M n-BuLi in hexane dropwise. After 30 minutes, this solution was transferred by cannula to a stirred −78° solution of 2,3,4,6-tetra-O-benzyl-β-D-glucolactone (0.39 g, 0.71 mmol) in 5 mL of THF. The solution was stirred for 2 hr at −78° prior to quenching with saturated aq. NH₄Cl. After warming to 20°, the reaction was diluted 2 fold with H₂O prior to 3 extractions with EtOAc. The combined EtOAc fractions were washed with brine and dried over Na₂SO₄. After concentration using a rotary evaporator, the residue was chromatographed on silica gel using 20% EtOAc/hexane to elute 142 mg of the desired title lactol.

D.

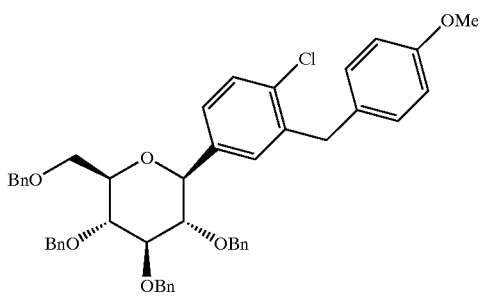

To a stirred −40° solution of Part C lactol (142 mg, 0.18 mmol) in 1.5 mL of MeCN was added iPr₃SiH (0.041 mL, 0.2 mmol) followed by BF₃·Et₂O (0.026 mL, 0.2 mmol). After 2 hr at −40°, when tlc showed the reaction to be complete, saturated aq. NaHCO₃ was added and the diluted with H₂O and CH₂Cl₂. The combined organic layers from 3 CH₂Cl₂ extractions were washed with brine, dried over Na₂SO₄, and concentrated using a rotary evaporator/ Chromatography of the residue on silica gel using 25% EtOAc/hexane as eluant eluted 139 mg of the desired beta C-arylglucoside.

E.

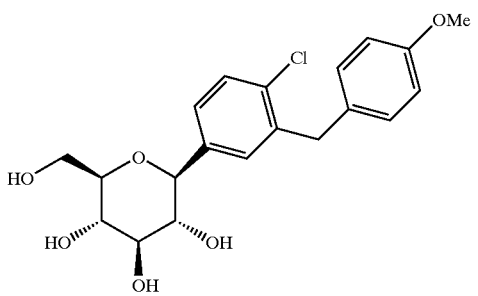

A solution of Part D tetra-O-benzyl C-glucoside (136 mg, 0.18 mmol) in EtSH (1.0 mL) containing BF₃·Et₂O (0.46 mL, 3.6 mmol) was stirred at 20° for 4 hr. The reaction was diluted with CH₂Cl₂ and then concentrated using a rotary evaporator. The residue, after being dissolved in CH₂Cl₂, was washed with aq. NH₄Cl, H₂O, brine, dried over Na₂SO₄, and concentrated using a rotary evaporator. The crude product was purified by preparative HPLC using a C₁₈ reverse phase column to obtain 26 mg of the desired beta C-glucoside as a white lyophilate after lyophilization.

HPLC retention time: 3.07 min, 95% pure, YMC S5 C-18 4.6×50 mm column, 2.5 mL/min, detection at 220 nM; 4 min gradient 0–100% B hold 4 min at 100% B. Solvent A: 10% MeOH/H₂O+0.2% H₃PO₄. Solvent B: 90% MeOH/H₂O+ 0.2% H₃PO₄. ¹H NMR (500 MHz, CD₃OD) δ 7.35–7.28 (m, 3H), 7.1 (d, 2H, J=8.8 Hz), 6.8 (d, 2H, J=8.3 Hz), 4.05–3.90 (m, 3H), 3.80 (d, 1H, J=12.3 Hz), 3.67 (s, 3H), 3.61 (dd, 1H, J=4.8, 11.9 Hz), 3.42–3.25 (m, 4H) Hz). ¹³C NMR (125 MHz, CD₃OD) δ 159.6, 140.0, 139.9, 134.5, 133.0, 131.9, 130.8, 130.1, 114.8, 82.9, 82.2, 79.8, 76.5, 71.9, 63.1, 55.6, 39.2. Anal. Calcd. for C₂₀H₂₃ClO₆ LC-MS [M+NH₄] 412. found 412.

EXAMPLE 13

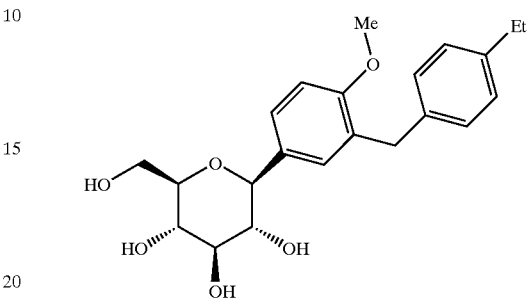

A. 5-Bromo-2-methoxy-4'-ethylbenzhydrol

To a stirred −78° solution of p-bromoethylbenzene (2.03 g, 11 mmol) in 10 mL of dry THF under Ar was added 5 mL of 2.5 M n-BuLi (12 mmol) in hexane over 10 min. The temperature was allowed to rise to −10° over 2 hr whereupon the reaction was cooled to −78° before adding solid 5-bromo-2-methoxybenzaldehyde (2.15 g, 10 mmol). After stirring overnight at 20°, the reaction was quenched with saturated aq. NH₄Cl and diluted 5 fold with H₂O prior to 3 extractions with EtOAc. The combined EtOAc fractions were washed with brine and dried over Na₂SO₄. After concentration using a rotary evaporator, the residue was chromatographed on silica gel using 10% EtOAc/hexane to elute 1.44 g of 5-bromo-2-methoxy-4'-ethylbenzhydrol.

B. 5-Bromo-2-methoxy-4'-ethyldiphenylmethane

A 9 mL solution of 1:8 CH₂Cl₂/MeCN containing crude Part A 5-bromo-2-methoxy-4'-ethylbenzhydrol (1.44 g, 4.5 mmol), Et₃SiH (0.75 mL, 5 mmol), and BF₃·Et₂O (0.6 mL, 6.4 mmol) was stirred overnight at 20°. After quenching with saturated aq. NaOH, the mixture was extracted 3×with EtOAc. The combined EtOAc fractions were washed with brine and dried over Na₂SO₄. After concentration using a rotary evaporator, the residue was chromatographed on silica gel using 2% EtOAc/hexane to elute 1.28 g of 5-bromo-2-methoxy-4'-ethyldiphenylmethane.

C.

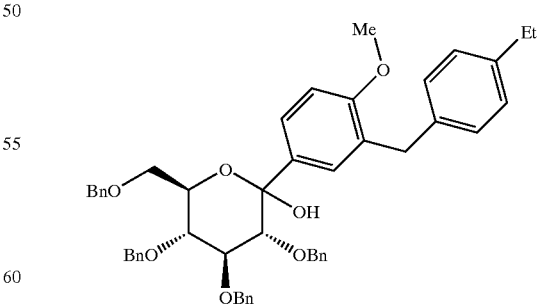

To a stirred −78° solution of Part B 5-bromo-2-methoxy-4'-ethyldiphenylmethane (0.25 g, 0.82 mmol) in 7 mL of dry THF under Ar was added dropwise 0.5 mL of 1.8 M n-BuLi in hexane. After 2 hr, 2,3,4,6-tetra-O-benzyl-β-D-glucolactone (0.48 g, 0.9 mmol) in 3 mL of THF was added over 1 min. The solution was stirred for 2 hr at −78° prior to quenching with saturated aq. NH₄Cl. After warming to 20°, the reaction was diluted 5 fold with H₂O prior to 3 extractions with EtOAc. The combined EtOAc fractions were washed with brine and dried over Na₂SO₄. After concentration using a rotary evaporator, 0.67 g of the desired title lactol was obtained as a light yellow syrup that was carried forward without further purification.

D.

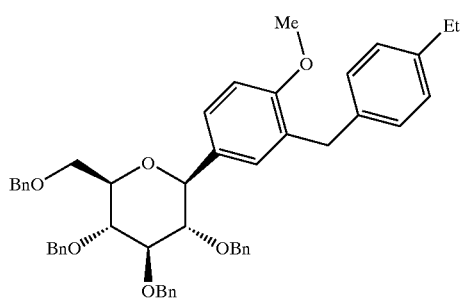

To a stirred −30° solution of Part C lactol (450 mg, 0.59 mmol) in 10 mL of MeCN was added iPr₃SiH (0.2 mL, 0.9 mmol) followed by BF₃·Et₂O (0.1 mL, 0.7 mmol). After 1.5 hr at −40°, the reaction being complete by tlc was quenched by addition of aq. NaHCO₃ an subsequently extracted 3× with EtOAc. The combined organic layers were washed with brine, dried over Na₂SO₄, and concentrated using a rotary evaporator. Chromatography of the residue on silica gel with 10% EtOAc/hexane eluted 320 mg of the desired beta C-arylglucoside.

E.

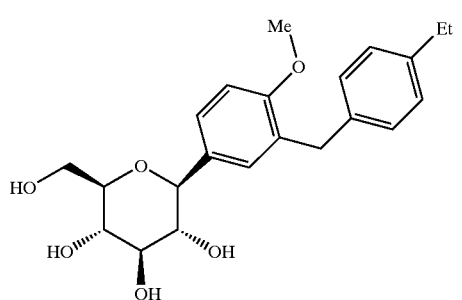

A solution of Part D tetra-O-benzyl C-glucoside (320 mg, 0.7 mmol) in EtOAc (15 mL) containing 10% Pd(OH)₂/C (30 mg) was stirred overnight under 1 atmos. H₂. After HPLC showed the reaction to be complete, the catalyst was filtered and the solvent removed using a rotary evaporator. The crude product was further purified by preparative HPLC using a C₁₈ reverse phase column to obtain 24 mg of the desired beta C-glucoside as a white solid after lyophilization.

HPLC retention time: 3.84 min, 95% pure, YMC S5 C-18 4.6×50 mm column, 2.5 mL/min, detection at 220 nM; 4 min gradient 0–100% B hold 4 min at 100% B. Solvent A: 10% MeOH/H₂O+0.2% H₃PO₄. Solvent B: 90% MeOH/H₂O+ 0.2% H₃PO₄. ¹H NMR (500 MHz, CD₃OD) δ 7.23 (d, 1H, J=7 Hz), 7.17 (s, 1H), 7.05 (ABq, 4H), 6.89 (d, 1H, J=7 Hz), 4.02 (d, 1H J=9 Hz), 3.92–3.83 (m, 3H), 3.76 (s, 3H), 3.66 (dd, 1H), 3.45–3.29 (m, 4H), 2.55 (q, 2H), 1.16 (t, 3H). Anal. Calcd. for C₂₂H₂₈O₆ LC-MS [M+NH₄] 406. found 406.

EXAMPLE 14

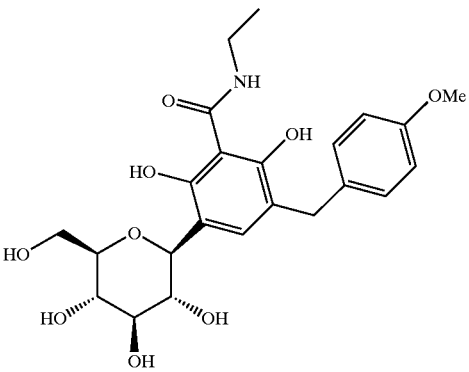

A. N-Ethyl-N-4-methoxybenzyl-2,6-dihydroxybenzamide

To a stirred solution of N-ethyl-4-methoxybenzyl amine (1.07 g, 6.49 mmol) in DMF (10 mL) was added 2,6-dihydroxybenzoic acid (1.0 g, 6.49 mmol) followed by HOAt (0.97 g, 7.14 mmol) and EDC (1.31 g, 6.81 mmol). After stirring overnight, the reaction was diluted with EtOAc prior to washing 3× with H₂O. The combined aqueous layers were extracted once with EtOAc. The organic fractions were combined, washed once with brine, and dried over Na₂SO₄ prior to concentrating using a rotary evaporator. The residue was chromatographed on silica gel using 75% EtOAc/hexane as the eluent. The resulting promising impure fractions were further purified by silica gel chromatography. A total of 631 mg of the desired N-ethyl-N-4-methoxybenzyl 2,6-dihydroxybenzamide was obtained.

B.

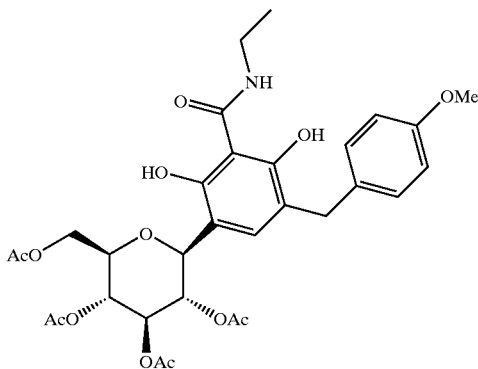

A stirred suspension of the Part A amide (630 mg, 2.09 mmol), CdCO₃ (939 mg, 5.44 mmol) in toluene (30 mL) was refluxed for 1.5 hr using a Dean Stark trap prior to the addition of 2,3,4,6-tetra-O-acetyl-α-D-glucosopyranosyl bromide (1.12 g, (2.72 mmol). After 15 hr of reflux, no starting amide remained by tlc analysis. The hot suspension was filtered through celite which was washed with hot PhMe and then 3× with hot CHCl₃. After removal of the volatiles using a rotary evaporator, the residue was chromatographed on silica gel. A mixture of O-glucosides was eluted with 1:1 EtOAc/hexane prior to the tetraacetate of the desired title C-glucoside; 172 mg of severely contaminated title C-glucoside was obtained.

C.

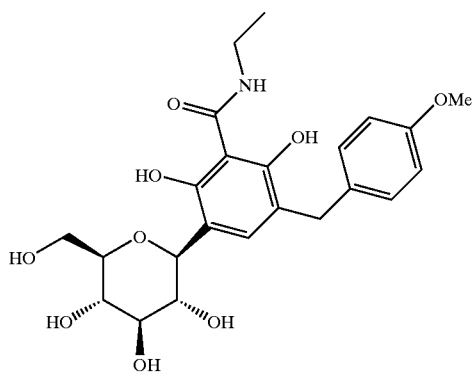

Impure Part B ester was stirred in 6:1 EtOH/H$_2$O (1.4 mL) containing KOH (140 mg, 2.5 mmol) for 16 hr. The resulting solution was cooled to 4°, acidified to pH 5, and then extracted 2× with EtOAc. The combined EtOAc layers were washed with brine, and dried over Na$_2$SO$_4$ prior to concentrating using a rotary evaporator. The residue was purified by prep HPLC with a C$_{18}$ YMC reverse phase column using a 45–90% MeOH/H$_2$O gradient over 30 min to elute the desired title C-glucoside (7.8 mg).

HPLC: 99.1%; Shimadzu LC-6A, YMC S3 ODS (6.0× 150 mm); flow rate of 1.5 mL/min; detection at 220 nM; gradient elution 0–100% B over 30 minutes (A=90% H$_2$O, 10% MeOH, 0.2% H3PO4, and B=90% MeOH, 10% H$_2$O, 0.2% H3PO4); retention time=23.4 minutes. 1H NMR (400 MHz, CD$_3$OD): δ 1.22 (3H, t, J=7.2 Hz), 3.4–3.5 (6H, m), 3.73 (3H, s), 3.74 (1H, m), 3.77 (1H, m), 3.8–3.9 (2H,m), 4.36 (1H, d, J=9.3 Hz), 6.77 (2H, d, J=8.6 Hz), 7.11 (2H, d, J=8.6 Hz), 7.18 (1H, s) 13C NMR (125 MHz, CD$_3$OD): δ 14.9, 35.1, 35.1, 55.7, 62.5, 71.2, 75.8, 79.6, 80.3, 82.3, 104.8, 114.7, 117.1, 122.7, 130.7, 134.5, 134.6, 151, 159.3, 161, 171.9 Anal. Calcd. for C$_{23}$H$_{29}$NO$_9$ LC-MS [M−H] 462. found 462.

EXAMPLE 15

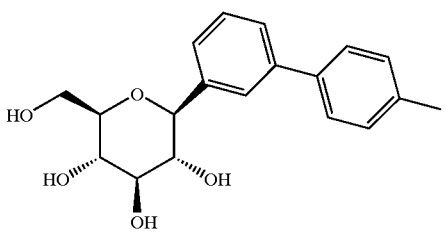

A.

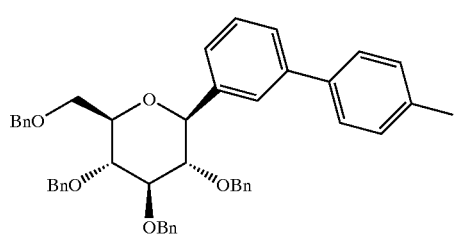

A mixture of Example 3 Part B β-m-bromophenyl-C-glucoside (100 mg, 0.14 mmol), p-methylphenylboronic acid (59 mg, 0.43 mmol), Na$_2$CO$_3$ (46 mg, 0.43 mmol), and Pd(PPh$_3$)$_4$ (153 mg, 0.13 mmol) in 3:1 PhMe/EtOH were stirred under Ar at 80° for 15 hr. After removal of the volatiles using a rotary evaporator, the residue was chromatographed on silica gel. 10:1 hexane/EtOAc eluted the desired title biphenyl C-glucoside (90 mg) as a clear oil.

B.

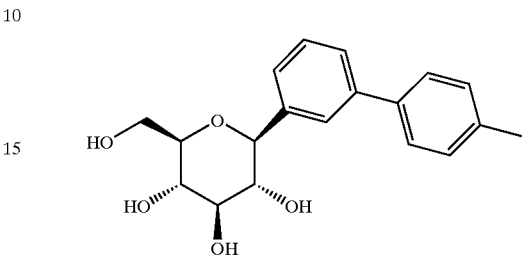

To a −78° stirred CH$_2$Cl$_2$ solution (0.4 mL) of Part A tetra-O-benzyl ether (65 mg, 0.09 mmol) under Ar was added 0.37 mL of a 1M BCl$_3$ in CH$_2$Cl$_2$. After 1 hr, the reaction was quenched with 2 mL of MeOH and allowed to warm to 20°. After adjusting the pH to 7 with aqueous NaHCO$_3$, the suspension was extracted 2× with CH$_2$Cl$_2$. The combined organic layers were dried over MgSO$_4$ and concentrated. The resulting residue, after purification by preparative HPLC using a C$_{18}$ reverse phase column, yielded 6.6 mg of final title product. (Note the product is partially destroyed by the strongly acidic medium generated after the MeOH quench of the BCl$_3$.)

HPLC retention time: 6.353 min, 100% pure, Zorbax C-18 4.6×50 mm, 2.5 mL/min, detection at 220 nM; 8 min gradient 0–100% B hold 5 min at 100% B. Solvent A: 10% MeOH/H$_2$O+0.2% H$_3$PO$_4$. Solvent B: 90% MeOH/H$_2$O+ 0.2% H$_3$PO$_4$. $^1$H NMR (400 MHz, CD$_3$OD) δ 7.65 (s, 1H), 7.53–7.50 (m, 3H), 7.39–3.37 (m, 2H), 7.23 (d, 2H, J=7.9 Hz), 4.20 (d, 1H, J=9.3 Hz), 3.89 (dd, 1H, J=2.2, 11.9 Hz), 3.71 (dd, 1H, J=5.7, 11.9 Hz), 3.50–3.40 (m, 4H), 2.36 (s, 3H) Anal. Calcd. for C$_{19}$H$_{22}$O$_5$ Low Res MS [M−H] 329. found 329.

EXAMPLES 16 TO 80

The compounds of Examples 16 to 80 set out in the following Tables 1 and 2 were prepared employing procedures of Examples 1 to 15 and reaction Schemes 1 to 9 above. It will be appreciated that compounds wherein A, which may linked at the ortho, meta, or para position of the aryl ring attached to the glucoside, may be any one of (CH$_2$)$_n$, O, NH or S while R$^1$, R$^2$, R$^{2a}$, R$^3$, and R$^4$ may be any of the substituents as defined above, may be prepared employing the procedures of Examples 1 to 15 and reaction Schemes 1 to 9.

TABLE 1

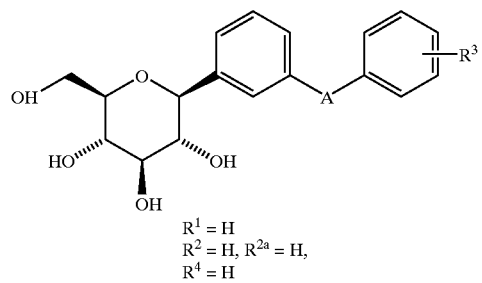

$R^1 = H$
$R^2 = H, R^{2a} = H,$
$R^4 = H$

| Example | A | $R^3$ | Method of Example # | LC/MS or MS $(M + H)^+$ |
|---|---|---|---|---|
| 16 | $CH_2$ | 4-Me | 1 | 345 |
| 17 | $CH_2$ | 4-OH | 1 | 347 |
| 18 | $CH_2$ | 3-Me | 2 | 345 |
| 19 | $CH_2$ | H | 3 | 331 |
| 20 | $CH_2$ | 3-OMe | 3 | 361 |
| 21 | $CH_2$ | 4-$CO_2$Me | 3 | 389 |
| 22 | $CH_2$ | 3,4-($OCH_2O$) | 3 | 375 |
| 23 | $CH_2$ | 4-$CF_3$ | 3 | 399 |
| 24 | $CH_2$ | 4-NHAc | 3 | 388 |
| 25 | $CH_2$ | 4-$SO_2$Me | 3 | 409 |
| 26 | $CH_2$ | 4-Ph | 3 | 407 |
| 27 | $CH_2$ | 4-$NHSO_2$Ph-4'-Me | 3 | 500 |
| 28 | $CH_2$ | 4-$NHSO_2$Me | 3 | 424 |
| 29 | $CH_2$ | 4-$CO_2$H | 3 | 375 |
| 30 | $CH_2$ | 4-Thiadiazole | 3 | 415 |
| 31 | $CH_2$ | 4-Tetrazole | 3 | 399 |
| 32 | $CH_2$ | 4-$OCH_2$Ph-4'-CN | 1 | 462 |
| 33 | $CH_2$ | 4-$OCHF_2$ | 1 | 397 |
| 34 | $CH_2$ | 4-iPr | 3 | 373 |
| 35 | $CH_2$ | 2-iPr | 3 | 373 |
| 36 | $CH_2$ | 4-O-nPr | 1 | 389 |
| 37 | $CH_2$ | 4-Tetrazole-2'-Me | 3 | 413 |
| 38 | $CH_2$ | 4-Tetrazole-1'-Me | 3 | 413 |
| 39 | $CH_2$ | 4-OPh | 1 | 423 |
| 40 | $CH_2$ | 4-nPr | 1 | 373 |
| 41 | $CH_2$ | 4-nBu | 1 | 387 |
| 42 | $CH_2$ | 4-$SO_2$Et | 1 | 423 |
| 43 | $CH_2$ | 4-$SO_2$-nPr | 1 | 437 |
| 44 | $CH_2$ | 4-$SO_2$Ph | 3 | 471 |
| 45 | $CH_2$ | 4-SOMe | 4 | 393 |
| 46 | Bond | H | 15 | 317 |
| 47 | Bond | 3-Me | 15 | 331 |
| 48 | Bond | 4-MeO | 15 | 347 |
| 49 | $(CH_2)_2$ | H | 1 | 343 (M − H) |
| 50 | $(CH_2)_2$ | 4-Me | 1 | 357 (M − H) |
| 51 | $(CH_2)_3$ | H | 1 | 376 (M + NH4) |
| 52 | $(CH_2)_3$ | 4-Me | 1 | 390 (M + NH4) |
| 53 | $(CH_2)_3$ | 3-Me | 1 | 390 (M + NH4) |
| 54 | Bond (para link) | H | 15 | 317 |
| 55 | $CH_2$ (ortho link) | H | 1 | 331 |
| 56 | $CH_2$ (ortho link) | 4-Et | 1 | 376 (M + NH4) |
| 57 | O | 4-Me | Scheme8 | 364 (M + NH4) |
| 58 | S | 4-Me | Scheme9 | 380 (M + NH4) |

TABLE 2

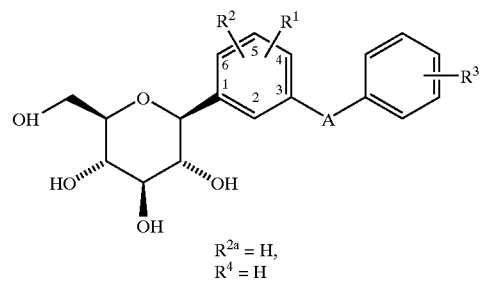

$R^{2a} = H,$
$R^4 = H$

| Example | A | $R^1$ | $R^2$ | $R^3$ | Method of Example # | LC/MS or MS $(M + H)^+$ |
|---|---|---|---|---|---|---|
| 59 | $CH_2$ | 2-Me | H | 4-Et | 1 | 371 (M − H) |
| 60 | $CH_2$ | 4-Me | H | 4-Et | 8 | 371 (M − H) |
| 61 | $CH_2$ | 4-Me | H | 4-$SO_2$Me | 8 | 445 (M + Na) |
| 62 | $CH_2$ | 4-Me | H | 4-OH | 9 | 359 (M − H) |
| 63 | $CH_2$ | 4-Me | H | 4-S(O)Me | 10 | 407 (M + H) |
| 64 | $CH_2$ | 4-Me | H | 4-F | 8 | 385 (M + NH4) |
| 65 | $CH_2$ | 4-Me | H | 4-Cl | 8 | 377 (M − H) |
| 66 | $CH_2$ | 4-Me | H | 4-Me | 8 | 357 (M − H) |
| 67 | $CH_2$ | 4-Me | H | H | 8 | 343 (M − H) |
| 68 | $CH_2$ | 4-Me | 6-Me | 4-OMe | 1 | 406 (M + NH4) |
| 69 | $CH_2$ | 4-F | H | 4-OMe | 1 | 396 (M + NH4) |
| 70 | $CH_2$ | 4-Cl | H | 4-SOMe | 11 | 427 (M + H) |
| 71 | $CH_2$ | 4-Cl | H | 4-$SO_2$Me | 11 | 441 (M − H) |
| 72 | $CH_2$ | 4-Cl | H | 4-$OCHF_2$ | 9 | 448 (M + NH4) |
| 73 | $CH_2$ | 4-Et | H | 4-OMe | 8 | 406 (M + NH4) |
| 74 | $CH_2$ | 4-iPr | H | 4-OMe | 8 | 420 (M + NH4) |
| 75 | $CH_2$ | 4-iPr | H | 4-SMe | 10 | 417 (M − H) |
| 76 | $CH_2$ | 4-iPr | H | 4-$SO_2$Me | 10 | 439 (M − H) |
| 77 | $CH_2$ | 4,5-$OCH_2O$ | H | 4-Et | 1 | 403 (M + H) |
| 78 | $CH_2$ | 5-Me | H | 4-Et | 1 | 390 (M + NH4) |
| 79 | $CH_2$ | 5-Me | 6-Me | 4-OMe | 1 | 406 (M + NH4) |
| 80 | $CH_2$ | 6-Me | H | 4-Et | 8 | 395 (M + Na) |

What is claimed:

1. A method for treating diabetes, diabetic retinopathy, diabetic neuropathy, diabetic nephropathy, insulin resistance, hyperglycemia, hyperinsulinemia, hyperlipidemia, obesity, hypertriglyceridemia or atherosclerosis via the inhibition of SGLT2 transporters which comprises administering to a mammalian species in need of treatment a therapeutically effective amount of a compound of formula I having the structure

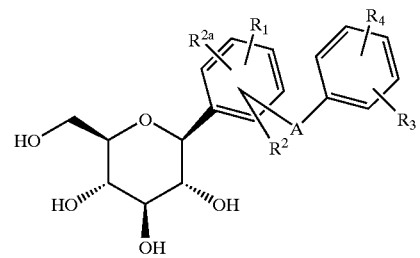

wherein
 $R^1$, $R^2$ and $R^{2a}$ are independently selected from the group consisting of hydrogen, OH, $OR^5$, alkyl, $CF_3$, $OCHF_2$, $OCF_3$, $SR^{5i}$ or halogen, or two of $R^1$, $R^2$ and $R^{2a}$ together with the carbons to which they are attached can form an annelated five, six or seven membered carbocycle or heterocycle which may contain 1 to 4 heteroatoms in the ring which are N, O, S, SO, and/or $SO_2$;

$R^1$ and $R^4$ are each independently selected from the group consisting of hydrogen, OH, $OR^{5a}$, OAryl, $OCH_2Aryl$, alkyl, cycloalkyl, $CF_3$, —$OCHF_2$, —$OCF_3$, halogen, —CN, —$CO_2R^{5b}$, —$CO_2H$, $COR^{6b}$, —$CH(OH)R^{6c}$, —$CH(OR^{5h})R^{6d}$, —$CONR^6R^{6a}$, —$NHCOR^{5c}$, —$NHSO_2R^{5d}$, —$NHSO_2Aryl$, Aryl, —$SR^{5e}$, —$SOR^{5f}$, —$SO_2R^{5g}$, —$SO_2Aryl$, and a five, six or seven membered heterocycle which may contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which may contain 1 to 4 heteroatoms in the ring which are N, O, S, SO, and/or $SO_2$;

$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;

$R^6$, $R^{6a}$, $R^{6b}$, $R^{6c}$, and $R^{6d}$ are are each independently selected from the group consisting of hydrogen, alkyl, aryl, alkylaryl and cycloalkyl, or $R^6$ and $R_{5a}$ together with the nitrogen to which they are attached form an annelated five, six or seven membered heterocycle which may contain 1 to 4 heteroatoms in the ring which are N, O, S, SO, and/or $SO_2$; and A is O or $(CH_2)_n$ where n is 0–3, or a pharmaceutically acceptable salt, stereoisomer, or prodrug ester thereof.

2. The method as defined in claim 1 comprising administering a therapeutically effective amount of a compound of formula I having the structure

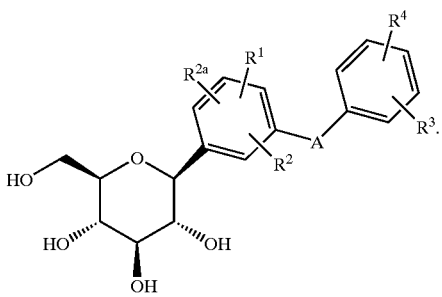

3. A method for treating diabetes, via the inhibition of SGLT2 transporters which comprises administering to a mammalian species in need of treatment a therapeutically effective amount of a compound of formula I having the structure

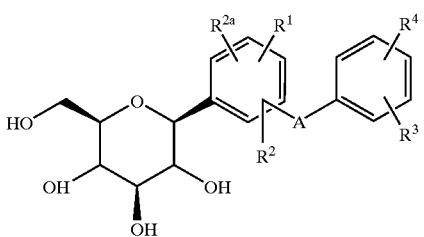

wherein $R^1$, $R^2$ and $R^{2a}$ are independently selected from the group consisting of hydrogen, OH, $OR^5$, alkyl, $CF_3$, $OCHF_2$, $OCF_3$, $SR^{5i}$ and halogen, or two of $R^1$, $R^2$ and $R^{2a}$ together with the carbons to which they are attached can form an annelated five, six or seven membered carbocycle or heterocycle which may contain 1 to 4 heteroatoms in the ring which are N, O, S, SO, and/or $SO_2$;

$R^3$ and $R^4$ are each independently selected from the group consisting of hydrogen, OH, $OR^{5a}$, OAryl, $OCH_2Aryl$, alkyl, cycloalkyl, $CF_3$, —$OCHF_2$, —$OCF_3$, halogen, —CN, —$CO_2R^{5b}$, —$CO_2H$, $COR^{6b}$, —$CH(OH)R^{6c}$, —$CH(OR^{5h})R^{6d}$, —$CONR^6R^{6a}$, —$NHCOR^{5c}$, —$NHSO_2R^{5d}$, —$NHSO_2Aryl$, Aryl, —$SR^{5e}$, —$SOR^{5f}$, —$SO_2R^{5g}$, —$SO_2Aryl$, and a five, six or seven membered heterocycle which may contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which may contain 1 to 4 heteroatoms in the ring which are N, O, S, SO, and/or $SO_2$;

$R^5$, $R^{5a}$, $R^{5b}$, $R^{5c}$, $R^{5d}$, $R^{5e}$, $R^{5f}$, $R^{5g}$, $R^{5h}$ and $R^{5i}$ are independently alkyl;

$R^6$, $R^{6a}$, $R^{6b}$, $R^{6c}$, and $R^{6d}$ are each independently selected from the group consisting of hydrogen, alkyl, aryl, alkylaryl and cycloalkyl, or $R^6$ and $R_{5a}$ together with the nitrogen to which they are attached form an annelated five, six or seven membered heterocycle which may contain 1 to 4 heteroatoms in the ring which are N, O, S, SO, and/or $SO_2$; and A is O or $(CH_2)_n$ where n is 0–3, or a pharmaceutically acceptable salt, stereoisomer, or prodrug ester thereof.

4. The method as defined in claim 1 comprising administering a therapeutically effective amount of a compound of formula I and at least one antidiabetic agent selected from the group consisting of metformin, glyburide, glimepiride, glipyride, glipizide, chlorpropamide, gliclazide, acarbose, miglitol, pioglitazone, troglitazone, rosiglitazone, insulin, isaglitazone, repaglinide and nateglinide.

5. The method as defined in claim 1 comprising administering a therapeutically effective amount of a compound of formula I and at least one anti-obesity agent selected from the group consisting of orlistat, sibutramine, topiramate, axokine, dexamphetamine, phentermine, phenylpropanolamine and mazindol.

6. The method as defined in claim 1 comprising administering a therapeutically effective amount of a compound of formula I and at least one lipid lowering agent selected from the group consisting of pravastatin, lovastatin, simvastatin, atorvastatin, cerivastatin, fluvastatin, nisvastatin, visastatin, atavastatin, rosuvastatin, fenofibrate, gemfibrozil, clofibrate and avasimibe.

7. The method as defined in claim 3 comprising administering a therapeutically effective amount of a compound of formula I and at least one antidiabetic agent selected from the group consisting of metformin, glyburide, glimepiride, glipyride, glipizide, chlorpropamide, gliclazide, acarbose, maglitol, pioglitazone, troglitazone, rosiglitazone, insulin, isaglitazone, repaglinide and nateglinide.

8. The method as defined in claim 3 comprising administering a therapeutically effective amount of a compound of formula I and at least one anti-obesity agent selected from the group consisting of orlistat, sibutramine, topiramate, axokine, dexamphetamine, phentermine, phenylpropanolamine and mazindol.

9. The method as defined in claim 3 comprising administering a therapeutically effective amount of a compound of formula I and at least one lipid lowering agent selected from the group consisting of pravastatin, lovastatin, simvastatin, atorvastatin, cerivastatin, fluvastatin, nisvastatin, visastatin, atavastatin, rosuvastatin, fenofibrate, gemfibrozil, clofibrate and avasimibe.

* * * * *